United States Patent
Bergeron, Jr.

(10) Patent No.: US 6,248,866 B1
(45) Date of Patent: *Jun. 19, 2001

(54) HYPUSINE REAGENT FOR PEPTIDE SYNTHESIS

(75) Inventor: Raymond J. Bergeron, Jr., Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/136,270

(22) Filed: Aug. 19, 1998

Related U.S. Application Data

(63) Continuation-in-part of application No. 08/962,300, filed on Oct. 31, 1997, now Pat. No. 5,973,113.

(51) Int. Cl.[7] .............................. C07K 5/00; C07K 7/00; C07C 229/00
(52) U.S. Cl. .................... 530/331; 530/333; 562/561; 562/562; 562/564
(58) Field of Search .................. 530/331, 333; 562/561, 562, 564

(56) References Cited

PUBLICATIONS

Abbruzzese et al., "Inhibition of deoxyhypusine hydroxylase by polyamines and by a deoxyhypusine peptide," *Biochim, Biophys, Acta*, pp. 997:248–255 (1989).
Bergeron, et al., "Development of a Hypusine Reagent For Peptide Synthesis", *J.Org.Chem.*, vol. 62, No. 10, pp.3285–3290 (1997).
Bergeron, et al., "Total Syntheses of (+) Hypusine and Its (2S,9S)–Diastereomer", *J.Org.Chem.*, vol. 58, No. 24, pp.6804–6806 (1993).
Bergmann, et al., "Uber ein all–gemeines Verfahren der Peptid–Synthese", *Ber.Dtsch.*, vol. 65, pp.1192–1201 (1932).
Bernady, et al., "Prostaglandins and Congeners.20. Synthesis of Prostaglandins via Conjugate Addition of Lithium trans–1–Alkenyltrialkylalanate Reagents. A Novel Reagent for Conjugate 1,4–Additions", *J.Org.Chem.*, vol.44, pp.1438–1447 (1979).
Beyermann, et al., "Rapid Continuous Peptide Synthesis via FMOC Amino Acid Chloride Coupling and 4–(Aminomethyl)piperidine Deblocking", *J.Org.Chem.*, vol. 55, pp.721–728 (1990).
Borch, et al., "The Cyanohydridoborate Anion as a Selective Reducing Agent", *J.Am.Chem.Soc.*, vol. 93, pp.2897–2904 (1971).
Mehta, et al., "Improved Efficiency and Selectivity in Peptide Synthesis: Use of Triethylsilane as a Carbocation Scavenger in Deprotection of t–Butyl Esters and t–Butoxycarbonyl–Protected Sites", *Tetrahedron Lett.*, vol.33, pp.5441–5444 (1992).
Stewart, et al., "Protection of the Hydroxyl Group in Peptide Synthesis", in *The Peptides*, Gross, et al., eds., Academic Press, New York, vol.3, pp.169–201 (1981).
Tarbell, et al., "New Method to Prepare N–t–Butoxycarbonyl Derivatives and the Corresponding Sulfur Analogs from di–t–Butyl Dicarbonate or di–t–Butyl Dithiol Dicarbonates and Amino Acids", *Proc.Natl.Acad,Sci,USA*, vol.69, pp.730–732 (1972).
Wang, et al., "Cleavage and Deprotection of Peptides on MBHA–Resin With Hydrogen Bromide", *Int.J.Peptide & Protein Res.*, vol.40, pp.344–349 (1992).

*Primary Examiner*—Bennett Celsa
(74) *Attorney, Agent, or Firm*—Hamilton, Brook, Smith & Reynolds, P.C.

(57) ABSTRACT

A derivative of hypusine useful as a reagent for synthesizing peptides containing hypusine, as well as an improved method for synthesizing the same, the derivative having the formula:

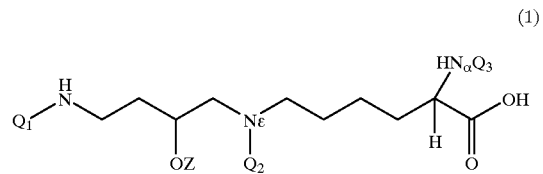

(1)

wherein: $Q_1$ and $Q_2$ may be the same or different and are amino protective groups; $Q_3$ is an amino protective group which is orthogonal to $Q_1$ and $Q_2$; and Z is a hydroxy protective group.

13 Claims, 6 Drawing Sheets

HYPUSINE REAGENT FOR PEPTIDE SYNTHESIS

CROSS REFERENCE TO RELATED APPLICATIONS

This application is a continuation-in-part of U.S. application Ser. No. 08/962,300, filed Oct. 31, 1997 now U.S. Pat. No. 5,973,113.

FIELD OF THE INVENTION

The present invention relates to novel hypusine derivatives useful as reagents for synthesizing peptides containing hypusine.

BACKGROUND OF THE INVENTION

Description of the Prior Art

Hypusine [$N_\epsilon$-(4-amino-2-hydroxybutyl)lysine], an unusual naturally occurring amino acid, having the structure:

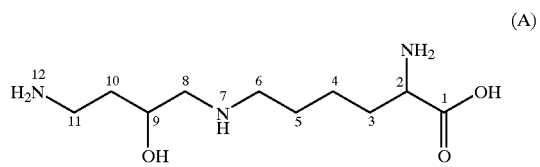

(A)

was first isolated from bovine brain extracts by Shiba et al. in 1971 [*Biochim. Biophys. Acta.*, Vol. 244, pages 523–531 (1971)]. The molecule has two chiral centers, one at position 2 and one at position 9, each of which can be classified R or S by the Cahn-Ingold-Prelog method. The (2S,9R)-diastereomer (B), formed as a

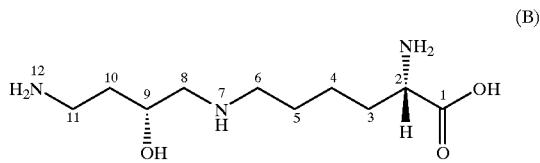

(B)

post-translational modification of lysine, has been shown to occur on a precursor protein of the eukaryotic initiation factor "eIF-5A" (formerly called eIF-4D or IF-$M_2$BX; the nomenclature for initiation factors having been revised) [Cooper et al., *Proc. Natl. Acad. Sci. USA*, Vol. 80, pages 1854–1857 (1983); and Safer, *Eur. J. Biochem.*, Vol. 186, pages 1–3 (1989)]. This initiation factor 5A is unique in that it is the only known cellular protein that contains the amino acid hypusine (Hpu). In the mid-1970's, eIF-5A was shown to stimulate ribosomal subunit joining and to enhance 80 S-bound Met-t-RNA reactivity with puromycin [Anderson et al., *FEBS Lett.*, Vol. 76, pages 1–10 (1977); and Kemper et al., *J. Biol. Chem.*, Vol. 251, pages 5551–5557 (1976)]. Later, in 1983, Cooper et al., supra, suggested that a hypusine-modified protein serves as an important initiation factor in all growing eukaryotic cells. In 1986, Park et al. [*J. Biol. Chem.*, Vol. 261, pages 14515–14519 (1986)] isolated the eIF-5A protein from human red blood cells and elucidated the amino acid sequence surrounding the single hypusine residue, as Thr-Gly-Hpu-His-Gly-His-Ala-Lys. Furthermore, and most interesting, because of the potential application to the control of HIV replication [Bevec et al., *Proc. Natl. Acad. Sci. USA*, Vol. 91, pages 10829–10833 (1994); and Ruhl et al. *J. Cell Biol.*, Vol. 123, pages 1309–1320 (1994)], the synthesis of eIF-5A analogues is of great therapeutic significance.

Since hypusine is specific to eIF-5A, antibodies derived from hypusine-containing peptides could be used to quantitate the levels of eIF-5A directly and with high specificity. Interest in developing an antibody assay of eIF-5A to investigate the physiological role of this important initiation factor prompted total synthesis of hypusine and its (2S,9R)-diastereomer [Bergeron et al., *J. Org. Chem.*, Vol. 58, pages 6804–6806 (1993)]. The key step in the synthesis involved the $N_\epsilon$-alkylation of $N_\epsilon$-benzyl-$N_\alpha$-carbobenzoxy-(L)-lysine benzyl ester with (R)- or (S)-epichlorohydrin to give the respective (2S,9R)- and (2S,9S)-chlorohydrins. Subsequent displacement of the respective chlorides by cyanide ion provided the protected hypusine skeletons. The final step, hydrogenation over $PtO_2$ in AcOH, followed by neutralization and re-acidification, yielded the respective (2S,9S)- and (2S,9R)-hypusine dihydrochlorides. A comparison of the reported hypusine optical rotation with that of the synthetic (2S,9R)-hypusine B confirmed the stereochemical integrity of both chiral centers throughout the synthesis.

Since there exists synthetic methodology for accessing hypusine itself, it would also be desirable to have a selectively protected hypusine reagent that could be used to incorporate this unusual amino acid into selected peptides.

It is an object of the present invention to provide such novel hypusine reagents, as well as methods for their synthesis.

SUMMARY OF THE INVENTION

These and other objects are realized by the present invention, one embodiment of which comprises a derivative of hypusine useful as a reagent for synthesizing peptides containing hypusine, the derivative having the formula:

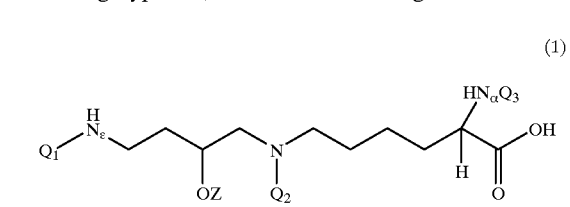

(1)

wherein: $Q_1$ and $Q_2$ may be the same or different and are amino protective groups; $Q_3$ is an amino protective group which is orthogonal to $Q_1$ and $Q_2$; and Z is a hydroxy protective group.

An additional embodiment of the invention relates to a method for synthesizing a hypusine reagent as defined above comprising:

a. providing an ester of $N_\epsilon$-, $N_\alpha$-diprotected L-lysine, the ester having the formula:

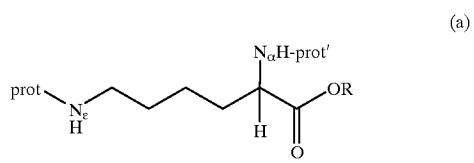

(a)

wherein prot and prot' are N-protective groups which are mutually orthogonal and R is the residue of an esterifying alcohol which is orthogonal with respect to prot and prot', b. removing prot from $N_\epsilon$ of (a) to produce a compound of the formula:

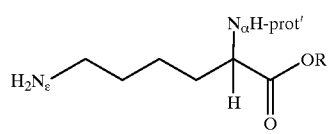

c. converting (b) to a compound of the formula:

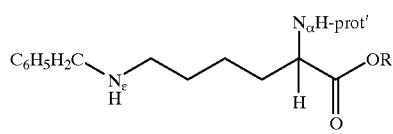

d. converting (c) a chlorohydrin of the formula:

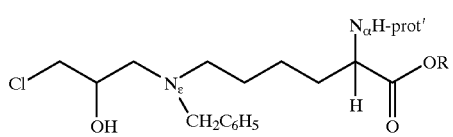

e. displacing the Cl group of (d) with CN to produce a nitrile of the formula:

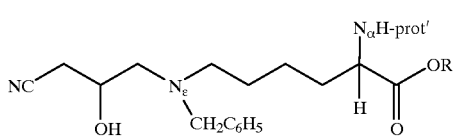

f. debenzylating the $N_\epsilon$ group and converting the CN group of (e) to an amine group to produce an amino alcohol of the formula:

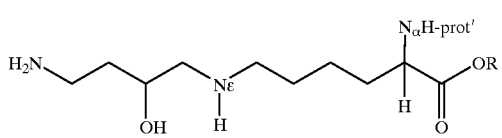

g. acylating the free amino groups of (f) to provide a di-N-protected $N_\epsilon$-protected L-lysine ester of the formula:

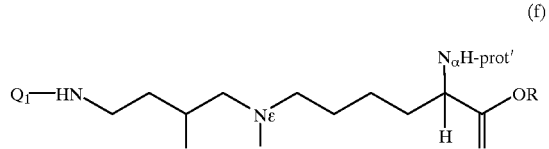

h. removing R and prot' from (g) to produce a compound of the formula:

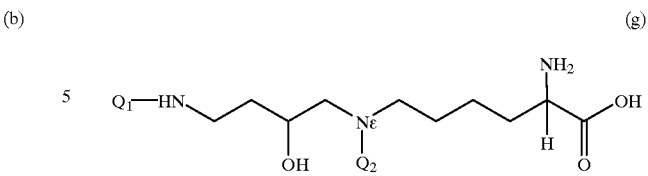

and i. acylating the free amino group and protecting the OH group to produce the hypusine derivative (1).

A further embodiment of the invention relates to an alternate method for synthesizing the hypusine reagent, wherein:

j. converting the compound of formula (b) to a chlorohydrin of the formula:

k. converting the compound of formula (j) to an $N_\epsilon$-protected chlorohydrin of the formula:

l. displacing the Cl group of (k) with CN to produce a nitrile of the formula:

m. deprotecting the $N_\epsilon$ group and converting the CN group of (l) to an amine group to produce the amino alcohol of the formula (f), followed by steps g, h, and i as above produces the hypusine derivative (1).

DETAILED DESCRIPTION OF THE INVENTION

Figure 1A:
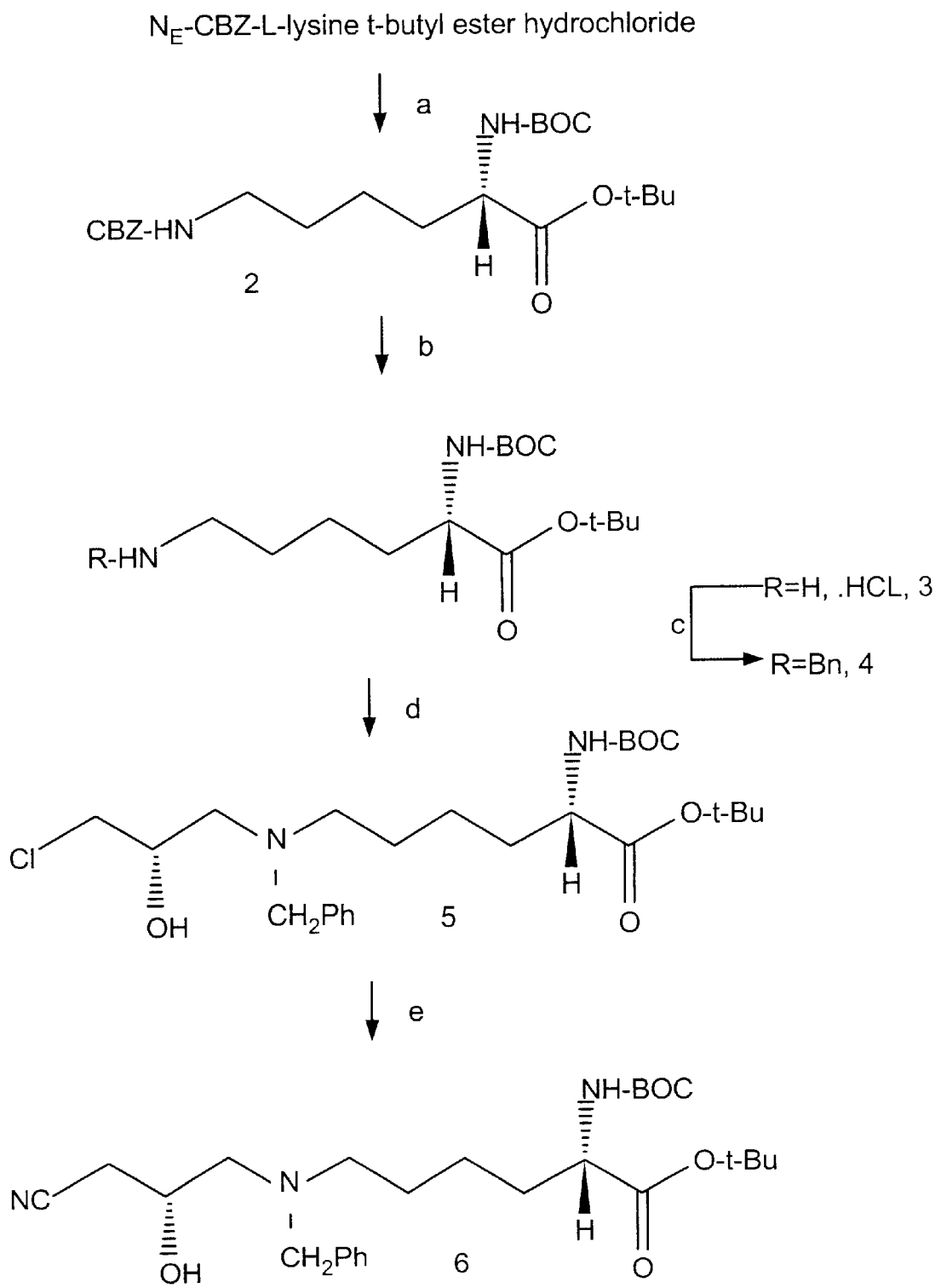
FIGS. 1a and b is a depiction of a reaction scheme for synthesizing the hypusine reagent of the invention. Reagents: (a) $(BOC)_2O$, $NaHCO_3$; (b) $H_2$, Pd—C; (c) PhCHO, $NaBH_3CN$; (d) (S)-(+)-epichlorohydrin, $MgSO_4$; (e) KCN, 18-crown-6; (f) $H_2$, Pd—C, $PtO_2$; (g) CBZ-Cl, DIEA; (h) TFA, triethylsilane, $CH_2Cl_2$; (i) 3,4-dihydro-2H-pyran; (j) FMOC-ONSu, $Na_2CO_3$.

In the preceding and subsequent descriptions of the present specification, suitable examples and illustrations of the various definitions which the present invention includes within the scope thereof are explained in detail as follows.

The expression "amino protective group" as used herein is intended to designate groups ($Q_1$, $Q_2$ and $Q_3$) which are inserted in place of a hydrogen atom of an amino group or groups in order to protect the amino group(s) during synthesis.

Selection of a suitable amino protecting group will depend upon the reason for protection and the ultimate use of the protected product. When the protecting group is used solely for protection during synthesis, then a conventional amino protecting group may be employed. Appropriate amino protecting groups are known in the art and are described, for example, by Bodanszky in *Principles of Synthesis,* Springer-Verlag, New York (1984); by Ives in U.S. Pat. No. 4,619,915; and in the various publications on peptide chemistry referred to in the latter. See also *Methoden der Organischen Chemie,* Houben-Weyl, Vol. 15, No. 1, for protecting groups and Vol. 15, No. 2, for methods of peptide synthesis. Representative amino protecting groups for synthetic use include acyl groups such as tert-butoxycarbonyl, benzyloxycarbonyl, fluorenylmethoxycarbonyl (FMOC), benzoyl, acetyl and the like. Yet other conventional amino protecting groups for use in synthesis are described in the literature [Bodanszky, supra, and Ives, supra].

The expression "hydroxyl protective group" as used herein is intended to designate a group (Z) which is inserted in place of a hydrogen atom of an OH group or groups in order to protect the OH group(s) during synthesis.

The preferred hydroxyl protective groups are the ethers, with the most preferred being the tetrahydropyranyl ether.

The term "orthogonal" when used herein to modify the term "protective group(s)" is intended to designate those protective groups in the molecule which are capable of being selectively removed from the molecule in the presence of other protective groups in the molecule without affecting the latter.

The various protecting groups for hydroxyl and amino functions discussed above can be substituted for the hydroxyl and amino functions in the instant amino acids/peptides (or their precursor molecules) by methods well known in the art. Methods for chemical removal of the protecting groups (when such are not to be retained in the pharmaceutically useful end product) are likewise well known to the skilled artisan. Typically, amine-protecting groups are chemically removed by acidolysis (acid hydrolysis) or hydrogenation, depending on the particular protecting group employed. Hydroxyl and carboxyl protecting groups are typically removed chemically by acid or base hydrolysis. Protecting groups that are incorporated in the pharmaceutical end product must be amenable to hydrolytic or metabolic cleavage in vivo.

The hypusine reagents of the present invention are useful as synthons for accessing peptides, in particular, the eIF-5A pentapeptide sequence. Thus, peptides incorporating hypusine may be prepared by sequential addition to an amino acid or to a protected amino acid, or by the addition of the reagent to an amino terminus free peptide. Thus, the reagent can be inserted directly into a dipeptide or larger fragment in the course of the peptide synthesis. At any point in the synthesis, the (X-nitrogen protecting group of the hypusine reagent can be removed and the carboxylate group of an amino acid, a protected amino acid, or a carboxylate free peptide coupled to it.

Methods for sequential addition of amino acids to form peptides, utilizing protecting groups where appropriate, are well known in the art. An excellent summary of such methods, including both solid phase synthesis and synthesis in solution, is contained in U.S. Pat. No. 4,530,920 (Nestor et al.) which is relied upon and incorporated by reference herein in its entirety. See also *Solid Phase Peptide Synthesis,* second edition, John Morrow Stewart and Janis Dillaha Young, eds., Pierce Chemical Company, Rockford, Ill. (1984). Peptides provided by the present invention can also be prepared by segment condensation methods described in the prior art (Bodanszky, supra, and *Methoden der Organischen Chemie,* supra).

Novel peptides incorporating hypusine produced via the method of the present invention are disclosed in a co-pending application entitled "Hypusine Peptides," filed as Attorney Docket No. SUNP-020/01US on Aug. 19, 1998, as a continuation-in-part application of U.S. Ser. No. 08/975, 656, filed Nov. 21, 1997, and in R. J. Bergeron et al., *J. Org. Chem.,* Vol. 62, 3285–3290 (1997), which disclosures are incorporated herein by reference.

Inspection of the structure of hypusine (A) reveals five potentially reactive centers: two primary amino and one secondary amino groups, a secondary hydroxyl group and a carboxyl group. In eIF-5A, the α-amino nitrogen (N2) required a protecting group which was orthogonal, i.e., removable under conditions different from those under which the groups masking N7 and N12 are removed, to those masking the other two potentially reactive amines (N7 and N12). Therefore, the N2 nitrogen was protected as, e.g., the N-fluorenylmethoxycarbonyl (N-FMOC) derivative, while the N7 and N12 amines were protected as, e.g., the N-carbobenzyloxy (N-CBZ) moieties. The 9-hydroxyl was masked as, e.g., a tetrahydropyranyl (THP) ether. This protection was necessary as the poorly reactive secondary hydroxyl was expected to cause difficulty with the anticipated N-acylating agents used in solid phase synthesis [Stewart, *The Peptides,* Vol. 3, page 170, Gross et al., eds., Academic Press, New York (1981)].

Figure 1B:
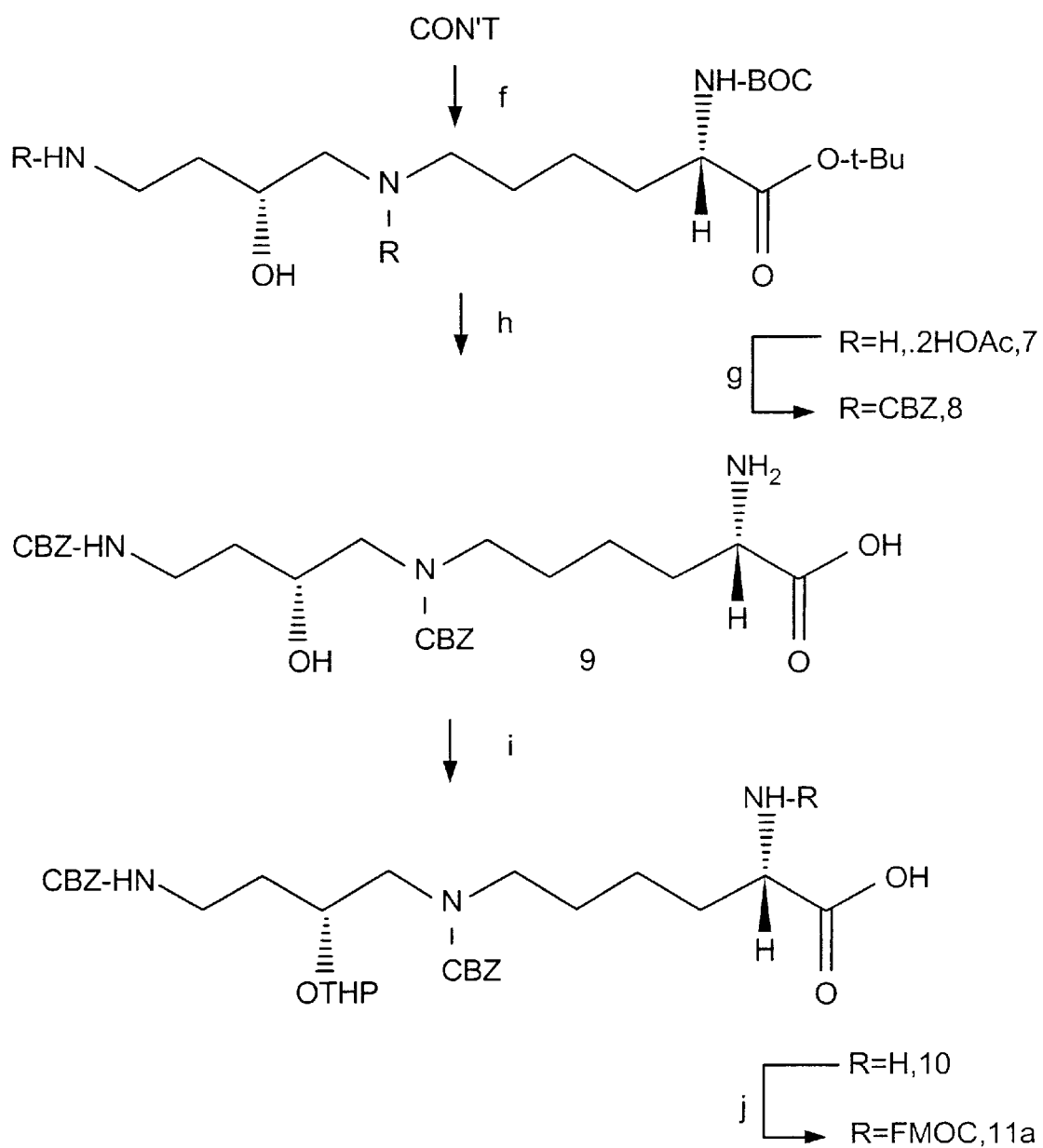

As shown in FIG. 1, the synthesis preferably begins with the t-butoxy-carbonylation (BOC) of $N_\epsilon$-CBZ-L-lysine t-Bu ester to give 2 in 98% yield [Tarbell et al., *Proc. Natl. Acad. Sci. USA,* Vol. 69, pages 730–732 (1972)].

The $N_\epsilon$-CBZ group of 2 was removed by hydrogenation over 10% Pd—C in ethanol and aqueous HCl to give 3 in 99% yield [Bergmann et al., *Ber. Dtsch.,* Chem. Abs., Vol. 65, pages 1192–1201 (1932)]. The $N_\epsilon$-benzyl-$N_\alpha$-BOC-L-lysine t-Bu ester 4 was synthesized from 3 by reductive amination of the liberated $N_\epsilon$ amine with benzaldehyde and sodium cyanoborohydride [Borch et al., *J. Am. Chem. Soc.,* Vol. 93, pages 2897–2904 (1971)].

The earlier synthesis of hypusine (Bergeron et al., supra) developed a chiral 4-amino-2-hydroxy butane synthon for accessing the parent molecule from an L-lysine derivative. In particular, this fragment made it possible to elaborate the $N_\epsilon$ benzyl group of a protected L-lysine into the N7–N12 structure of hypusine. In the synthesis of the present invention, this concept is further exploited. As shown in the reaction scheme depicted in FIG. 1, the subsequent $N_\epsilon$-alkylation of 4 with (S)-epichlorohydrin gave the (2S, 9S)-chlorohydrin (5). Displacement of the chloride ion (5) by cyanide ion afforded the protected (2S,9R)-hypusine skeleton (6). Debenzylation at N7 and conversion of the terminal nitrile in 6 was accomplished by hydrogenation to give the amino alcohol (7) as a diacetate. Acylation of the amino functions of amino alcohol (7) at N7 and N12 using CBZ groups as protecting groups provided di-CBZ-$N_\alpha$-t-BOC-(L)-lysine t-butyl ester (8). Selective removal of the t-butyl ester and $N_\alpha$-BOC protecting groups was accomplished with TFA and triethylsilane [Mehta et al., *Tetrahedron Lett.*, Vol. 33, pages 5441–5444 (1992)] to give the di-CBZ derivative 9. The secondary 9-hydroxyl function was protected as tetrahydropyranyl ether 10 [Bernady et al., *J. Org. Chem.*, Vol. 44, pages 1438–1447 (1979)] and subsequent acylation of the remaining $N_\alpha$-amine function with 9-fluorenylmethyl N-succinimidyl carbonate gave the hypusine reagent (11) with the desired protecting groups. Reagent (11) was converted to the dihydrochloride salt of (2S,9R)-hypusine (B) to give identical $^1$H NMR and comparable optical rotation as was cited in the art (Bergeron et al., supra) by removing the FMOC group with 4-aminomethyl-piperidine [Beyermann et al., *J. Org. Chem.*, Vol. 55, pages 721–728 (1990)] and deprotection of the remaining protecting groups following a method by Wang et al. [*Int. J. Peptide Res.*, Vol. 40, pages 344–349 (1992)].

In a similar fashion, hypusine reagent molecules of differing stereochemistries may be obtained in a like manner employing starting materials of opposite stereochemistries such as (R)-epichlorohydrin.

Figure 2A:
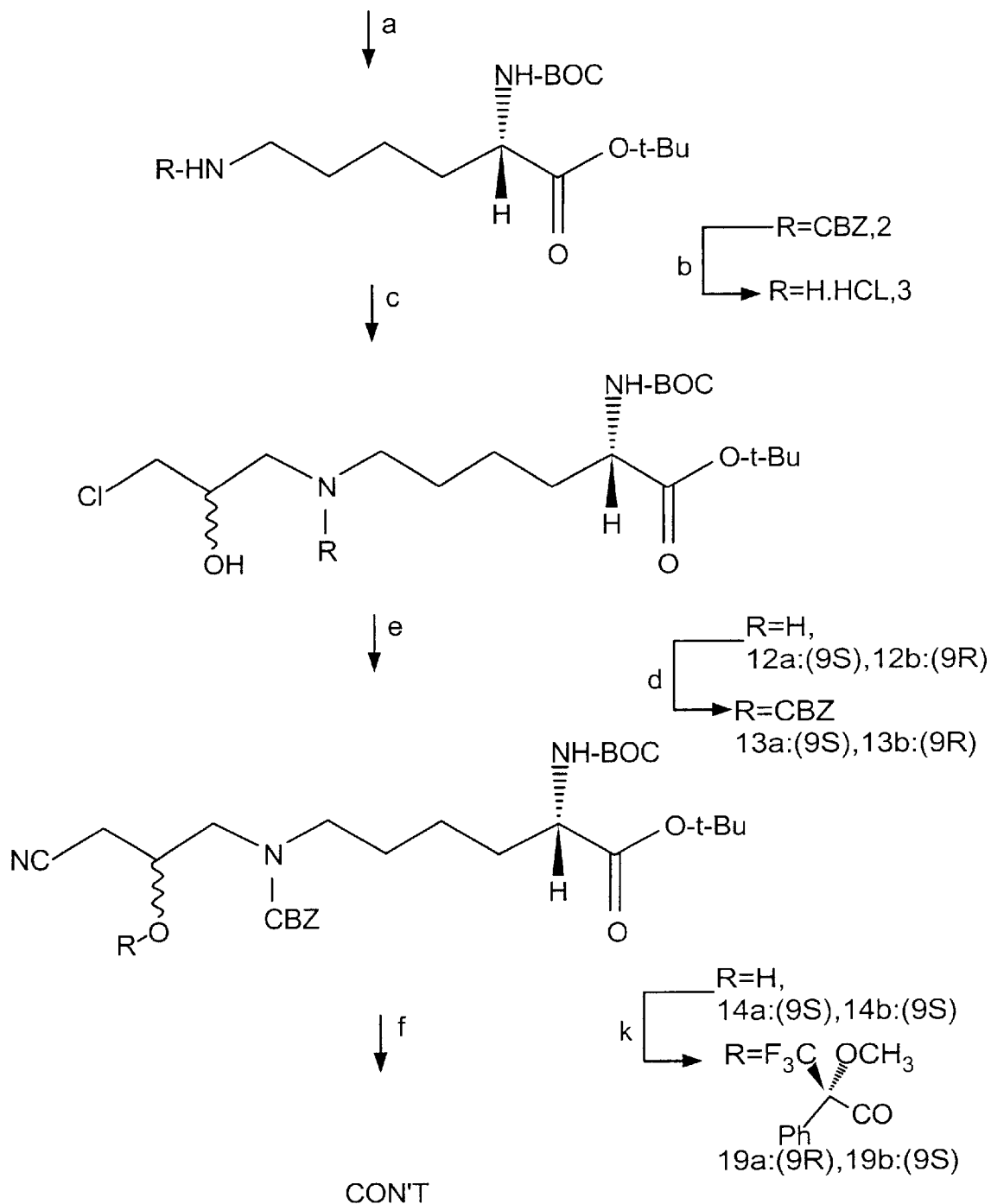
FIGS. 2a and b is a depiction of an alternate reaction scheme for synthesizing the hypusine reagent of the invention. Reagents: (a) $(BOC)_2O$, $NaHCO_3$; (b) $H_2$, Pd—C; (c) (S)-(+)- or (R)-(−)-epichlorohydrin, respectively; (d) benzyl chloroformate, triethylamine; (e) KCN, 18-crown-6; (f) $H_2$, Pd—C, $PtO_2$; (g) CBZ-ONSu, $KHCO_3$; (h) TFA, triethylsilane, $CH_2Cl_2$; (i) 3,4-dihydro-2H-pyran; 0) FMOC-ONSu, $Na_2CO_3$; (k) (R)-(−)-Mosher's acid chloride, pyridine.
Figure 2B:
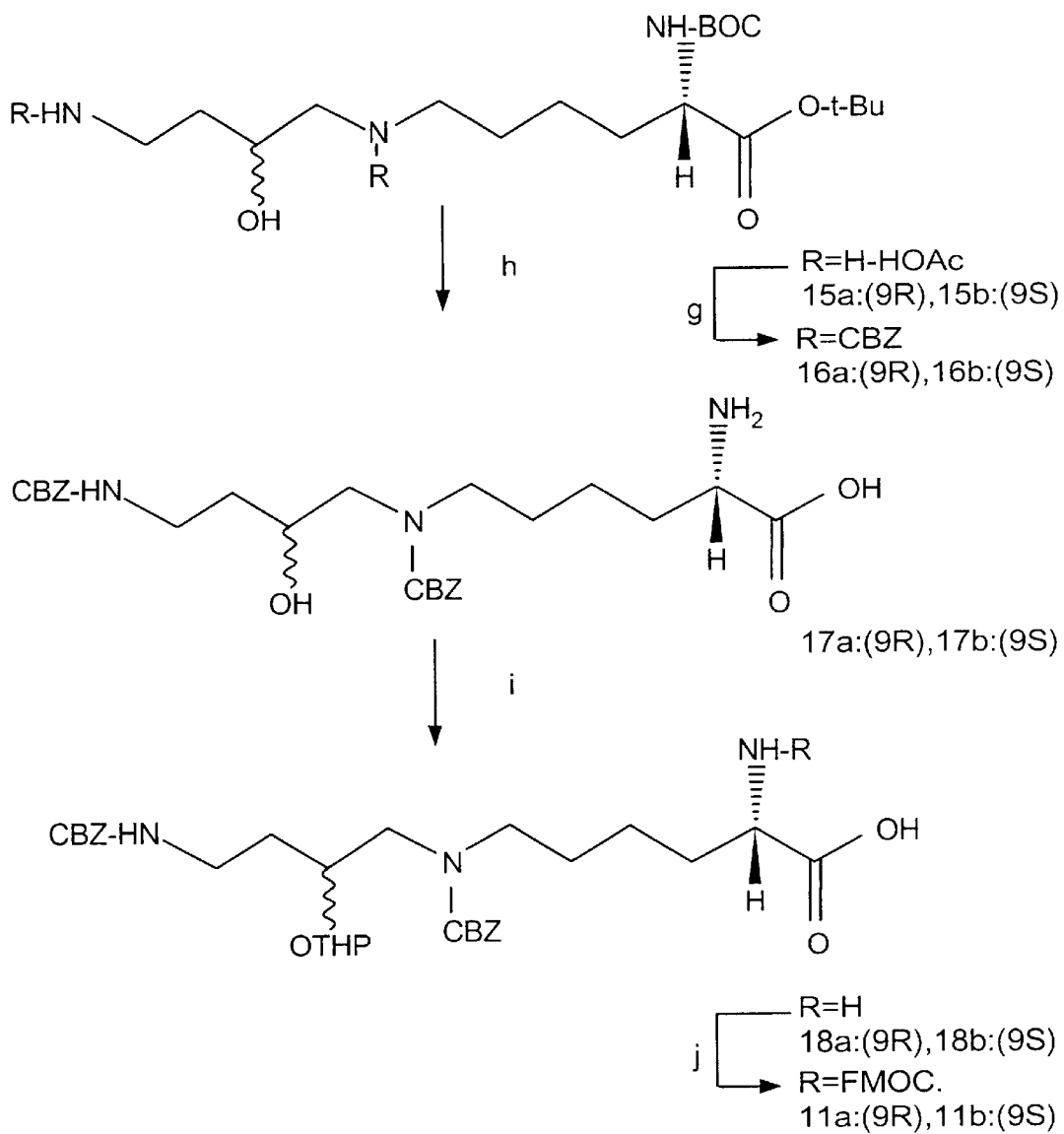

An alternate method for the synthesis of hypusine reagent 1 is preferred for scaled-up quantities, for example, to obtain greater than milligram quantities. A specific example of this method is illustrated in FIG. 2, which shows the synthesis of hypusine reagent 11a. This method avoids possible azetidinium salt formation, an intermediate that on cyanide opening could result in racemization at C-9. The method instead employs a halocarbamate intermediate (13a/b). Utilizing this approach, both the (2S,9R) reagent 11a and the corresponding (2S,9S) compound 11b were synthesized. Commercially available $N_\epsilon$-CBZ-L-lysine tert-butyl ester (FIG. 2) was protected with di-tert-butyl dicarbonate to yield [2], which was hydrogenated to remove the CBZ protecting group. The resulting primary amine [3] was reacted with either (S)-(+)-epichlorohydrin to generate the (9S)-chlorohydrin [(12a)] or with (R)-(−)-epichlorohydrin to produce the (9R)-chlorohydrin [(12b)]. Benzyl chloroformate was condensed with N-7 of the chlorohydrins, [12a and 12b], to yield the $N^7$-CBZ compounds [13a and 13b]. Again, because of the carbamate linkage at N-7, azetidinium formation is precluded. Reaction of [13a and 13b] with KCN in the presence of 18-crown-6 resulted in the corresponding nitriles [14a and 14b]. In each instance, the (9R)- and (9S)-hydroxy nitriles were converted to the Mosher esters [19a and 19b], respectively, in order to verify chiral integrity at C-9. The methoxy resonance in the $^1$H NMR spectrum of [19a] was observed at 3.60 ppm and in [19b] at 3.46 ppm. Both resonances were easily distinguishable in a mixture of the two compounds. The inability to observe the 3.46 ppm resonance of [19b] in the proton NMR of [19a] or the 3.60 ppm resonance of [19a in that of 19b] confirmed that chiral integrity at C-9 had been maintained to this stage in the synthetic sequence.

Nitriles [14a and 14b] were next reduced with hydrogen and a mixed catalyst. The resulting diamine diacetates, [15a and 15b], were then reacted with N-(benzyloxycarbonyloxy) succinimide (CBZ-ONSu) to produce the $N^7,N^{12}$-di-CBZ hydroxy derivatives [16a and 16b]. Treatment of these systems with trifluoroacetic acid and triethylsilane released both the BOC and tert-butyl ester protecting groups, resulting in the di-CBZ amino acids [17a and 17b]. The C-9 hydroxyl groups were next converted to the THP ethers [18a and 18b]. Finally, both [18a and 18b] were transformed to their FMOC derivatives [11a and 11b].

Figure 3A:
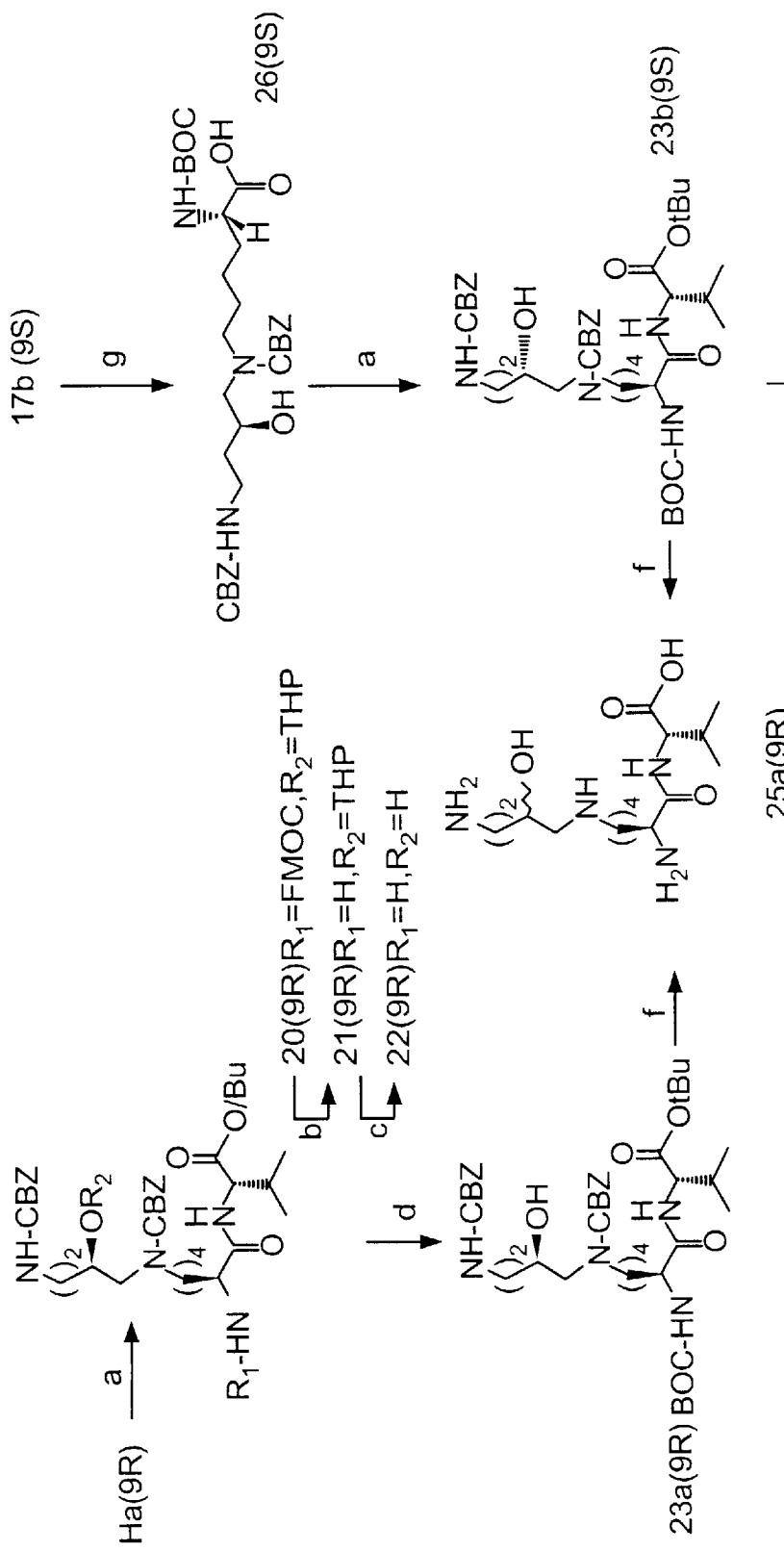
FIGS. 3a and 3b are a depiction of a verification of the stereochemical integrity of the hypusine reagent and its peptide products. Reagents: (a) L-valine t-butyl ester hydrochloride, BOP, DIEA; (b) piperidine; (c) pTosOH; (d) $(BOC)_2O$, $NaHCO_3$; (e) (R)-(−)-Mosher's acid chloride, pyridine; (f) HBr/HOAc in TFA, phenol, pentamethylbenzene, triisopropylsilane; (g) $(BOC)_2O$, NaOH.
Figure 3B:
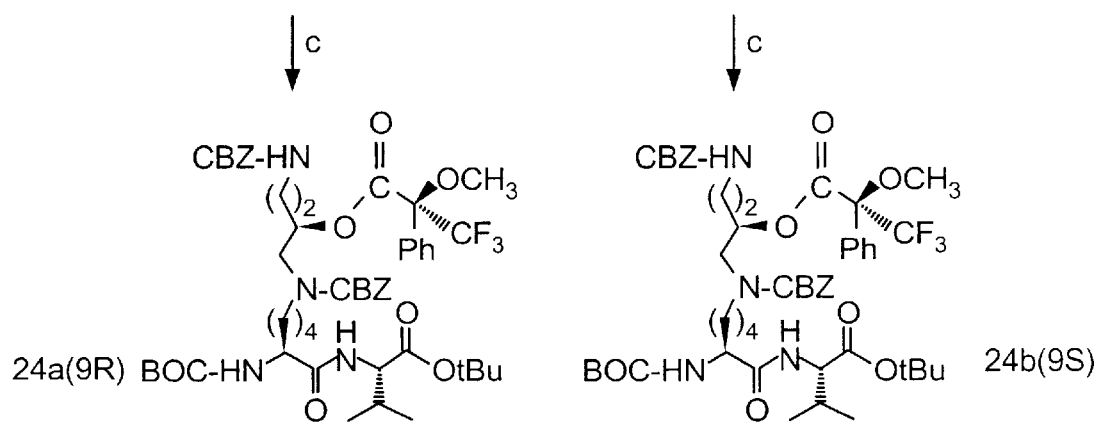

An additional verification of the stereochemical integrity of the reagent and its peptide products was undertaken (FIG. 3). In the course of earlier synthetic studies we demonstrated that the extent of racemization at the ($\alpha$-methine of the hypusine fragment may be quantified by preparing the corresponding L-valine dipeptide. Proton NMR spectra clearly distinguished between the L-lysyl-L-valine and D-lysyl-L-valine as well as between the related (2S,9R)-hypusinyl-L-valine and (2R,9R)-hypusinyl-L-valine dipeptide diastereomers. The protected hypusine reagent 11a (2S,9R) was condensed with valine tert-butyl ester resulting in the $\alpha$-N-FMOC-protected dipeptide [20] (2S,9R). The FMOC protecting group was next removed by exposure to piperidine, yielding [21], followed by p-toluenesulfonic acid in acetone-water to remove the THP ether (dipeptide [22]). Protection of the free nitrogen with BOC anhydride provided N$\alpha$-BOC dipeptide [23a] (2S,9R). This dipeptide [23a] was subjected to two separate reactions, conversion to Mosher ester [24a] (2S,9R) or deprotection using HBr in acetic acid/TFA/phenol/pentamethylbenzene/triisopropylsilane to dipeptide [25a] (2S,9R). To generate the other set of diastereomers (2S,9S), the $\alpha$-amino group of the di-CBZ intermediate [17b] (2S,9S) was reacted with BOC anhydride; the acid [26] thus generated was condensed with valine tert-butyl ester. As with [23a], two separate conversions were initiated: [23b] was transformed to the corresponding Mosher ester [24b] (2S,9S) and deprotected to yield dipeptide [25b] (2S,9S). Thus, three sets of diastereomers were available for comparison: [23a/b, 24a/b, and 25a/b]. Proton NMR spectra of [23a, 23b, 25a, and 25b] did not reveal the presence of any racemization at C-2 of the hypusine moiety as no (2R)-hypusinyl-L-valine diastereomers were detected. Furthermore, a comparison of both the $^1$H and $^{19}$F NMR analyses of [24a] (9R) and [24b] (9S) clearly supported the optical integrity at C-9. The Mosher ester methoxy protons and fluorine signals of [24a] (9R) occurred at δ 3.50 and −71.78 ppm, respectively, while the signals for [24b] (9S) were at δ 3.44 and −71.40 ppm.

EXAMPLES

The invention is illustrated by the following non-limiting examples which refer to the reaction schemes depicted in FIGS. 1–3, wherein $^1$H NMR spectra were recorded at 300 MHz unless otherwise specified; $^{13}$C NMR spectra were recorded at 75 MHz unless otherwise specified; chemical shifts are given in parts per million downfield from an internal tetramethylsilane or sodium 3-(trimethyl-silyl)-propionate standard; coupling constants (J) are given in Hz; mass spectra were carried out on a Kratos MS 80RFA or a Finnigan 4516 MS instrument; optical rotations were run at 589 nm (the Na D-line) on a Perkin-Elmer 341 polarimeter, with c expressed as grams of compound per 100 ml; and melting points were uncorrected. Chemical reagents were purchased from Aldrich, Fluka or Sigma Chemical Co. and used without further purification.

Example 1

N$_\alpha$-BOC-N$_\epsilon$-CBZ-L-Lysine tert-Butyl Ester (2)

Sodium hydrogen carbonate (2.81 g, 33.47 mmol) in water (75 ml) was added to H-Lys (CBZ)-O-t-Bu hydrochloride (12.00 g, 32.18 mmol) in chloroform (100 ml) and the mixture was stirred at room temperature for 5 minutes under an N$_2$ atmosphere. Di-tert-butyl dicarbonate (7.02 g, 32.18 mmol) in chloroform (50 ml) was added, the mixture was refluxed for 1.5 hours and allowed to cool to room temperature. The layers were separated, the aqueous layer was extracted with chloroform (3×100 ml) and the combined organic layers were dried over magnesium sulfate. Concentration in vacuo followed by flash chromatography (3:1 hexane:ethyl acetate) gave (2) (13.82 g, 98%) as a colorless oil. $^1$H NMR (CDCl$_3$) δ7.30 (s, 5H), 5.10(s,2H), 4.82 (m, 1H), 4.18 (m, 1H), 3.20 (m, 2H), 1.90–1.30 (m, 6H), 1.48 (s, 9H), 1.46 (s, 9H); $^{13}$C NMR (CD$_3$OD) δ 173.8, 158.8, 158.1, 138.4, 129.4, 128.9, 128.7, 82.5, 80.4, 67.3, 55.7, 41.4, 32.4, 30.4, 28.7, 28.3, 24.0. HRMS m/z calcd. For C$_{23}$H$_{37}$N$_2$O$_6$ 437.2652, found 437.2643. Anal. calcd. for C$_{23}$H$_{36}$N$_2$O$_6$: C 63.28, H 8.31, N 6.42. Found: C 63.13, H 8.28, N 6.47. [α]$^{27}$D+5.0° (c=2.00, CHCl$_3$).

Example 2

N$_\alpha$-BOC-L-Lysine tert-Butyl Ester Hydrochloride (3)

N$_\alpha$-BOC-NF-CBZ-L-lysine tert-butyl ester (2) (34.51 g, 79.15 mmol) was dissolved in a mixture of 300 ml absolute EtOH and 1 N HCl (88 ml). Prior to the introduction of H$_2$ gas, 10% Pd—C (2.95 g) was added. After 7 hours, additional catalyst (1.0 g) was added. After 5 hours, the black suspension was filtered through a bed of Celite and washed with EtOH. The filtrate was concentrated and the residue dried under high vacuum to give the N$_\alpha$-BOC-L-lysine tert-butyl ester as its hydrochloride salt (3) (26.59 g, 99%). $^1$H NMR (CD$_3$OD) δ 3.95 (dd, 1H, J=8.8, 5.0), 2.93 (t, 2H, J=7.7), 1.84–1.60 (m, 6H), 1.45 (s, 9H), 1.43 (s, 9H); $^{13}$C NMR (CD$_3$OD) δ 173.5, 158.2, 82.7, 80.5, 79.5, 55.5, 40.6, 32.1, 28.7, 28.3, 23.9. HRMS m/z calcd. for C$_{15}$H$_{31}$N$_2$O$_4$ 303.2284, found 303.2272. [α]$^{26}$$_D$–10.1° (c=1.00, CH$_3$OH).

Example 3

N$_\epsilon$Benzyl-N$_\alpha$-BOC-L-Lysine tert-Butyl Ester (4)

N$_\alpha$-BOC-L-lysine t-butyl ester hydrochloride salt (3) (25.97 g, 76.64 mmol) was dissolved in CHCl$_3$ (300 ml) and washed with saturated aqueous Na$_2$CO$_3$ solution (2×100 ml). The organic layer was separated, dried (MgSO$_4$), filtered and concentrated. The resultant oil (the free amine) was combined with benzaldehyde (10.42 g, 98.13 mmol), EtOH (150 ml) and activated 3 Å molecular sieves (46.0 g). The mixture was stirred under N$_2$ for 6 hours. Sodium cyanoborohydride (2.41 g, 38.4 mmol) was added, and the mixture was stirred overnight at room temperature. The brown mixture was filtered, and the filtrate was acidified to pH 2 with 1 N HCl (110 ml). The yellow solution was concentrated to dryness, dissolved in CHCl$_3$ and washed with saturated Na$_2$CO$_3$ solution and water. The organic layer was separated, dried (MgSO$_4$) and concentrated. Flash column chromatography (10% EtOH/CHCl$_3$, R$_f$=0.30) afforded the N$_\epsilon$-benzyl-N$_\alpha$-BOC-L-lysine t-butyl ester (4) (16.16 g, 54%) as a colorless oil. $^1$H NMR (CD$_3$OD) δ 7.34–7.20 (m, 5H), 3.91 (dd, 1H, J=9.0, 5.1), 3.72 (s, 2H), 2.58 (t, 2H, J=7.2), 1.82–1.30 (m, 6H), 1.45 (s, 9H), 1.43 (s, 9H); $^{13}$C NMR (CDCl$_3$) δ 171.9, 155.3, 140.1, 128.3, 128.1, 126.9, 81.6, 79.5, 53.9, 48.9, 32.7, 29.5, 28.3, 27.9, 22.9. HRMS m/z calcd. for C$_{22}$H$_{36}$N$_2$O$_4$ 392.2675, found 392.2676. Anal. calcd. for C$_{22}$H$_{36}$N$_2$O$_4$: C 67.32, H 9.24, N 7.14. Found: C 67.40, H 9.28, N 7.16. [α]$^{25}$$_D$=6.9° (c =1.00, CHCl$_3$).

Example 4

(2S,9S)-7-Benzyl-2-[(tert-butoxycarbonyl)amino]-10-chloro-9- hydroxy-7-azadecanoic Acid, tert-Butyl Ester (5)

A mixture of N$_\epsilon$-benzyl-N$_\alpha$-BOC-L-lysine t-butyl ester (4) (16.0 g, 40.76 mmol), CH$_3$OH (40 ml), (S)-(+)-epichlorohydrin (4.17 g, 45.0 mmol) and anhydrous MgSO$_4$ (5.33 g. 44.28 mmol) was stirred under N$_2$ for three days. The solids were filtered off and washed with CH$_3$OH. The filtrate was concentrated at room temperature to give a yellow oil. The resulting oil was purified by flash chromatography on silica gel (66% hexane/ethyl acetate) to give 13.23 g of (5) (77%) as a colorless oil. $^1$H NMR (C$_6$D$_6$) δ 7.18 (m, 5H), 5.00 (br d, 1H), 4.40 (m, 1H), 3.62 (m, 1H), 3.40–3.10 (m, 4H), 2.20–2.00 (m, 4H), 1.63 (m, 1H), 1.40 (s, 9H), 1.31 (s, 9H), 1.20 (m, 2H). $^{13}$C NMR (C$_6$D$_6$) δ 171.7, 155.2, 138.8, 128.8, 127.9, 127.0, 80.8, 78.8, 67.7, 58.8, 57.2, 53.9, 53.7, 47.3, 32.5, 28.0, 27.5, 26.3, 22.8. HRMS m/z calcd. for C$_{25}$H$_{42}$ClN$_2$O$_5$ 485.2782, found 485.2775. [α]$^{25}$$_D$+5.3° (c=1.00, CHCl$_3$).

Example 5

(2S,9R)-7-Benzyl-2-[(tert-butoxycarbonyl)amino]-10-cyano-9-hydroxy-7-azadecanoic Acid tert-Butyl Ester (6)

A mixture of (5) (6.99 g, 14.4 mmol), dry KCN (9.38 g, 144 mmol) and 18-crown-6 (0.76 g, 2.88 mmol) in 275 ml of dry acetonitrile was stirred at 45° C. for 5 days. It should be noted that heating this mixture to reflux causes significant decomposition. The reaction mixture was cooled, filtered and concentrated. Flash column chromatography on silica gel (25% ethyl acetate/hexane) gave the (2S,9R)-nitrile (6) as a colorless oil (4.82 g, 70%). $^1$H NMR (CD$_3$OD) δ 7.34–7.18 (m, 5H), 3.97–3.83 (m, 2H), 3.67 (dd, 1H, J=13.4, 2.6), 3.54 (dd, 1H, J=13.4, 4.0), 2.72– 2.40 (m, 6H), 1.80–1.50 (m, 4H), 1.45 (s, 9H), 1.44 (s, 9H), 1.40–1.30 (m, 2H). $^{13}$C NMR (CDCl$_3$) δ 171.8, 155.3, 138.1, 128.8, 128.4, 127.3, 117.1, 81.6, 79.5, 63.6, 58.8, 54.0, 32.6, 28.2, 27.9, 22.1. HRMS m/z calcd. for C$_{26}$H$_{42}$N$_3$O$_5$ 476.3124, found 476.3121. Anal. calcd. for C$_{26}$H$_{41}$N$_3$O$_5$. C 65.66, H 8.69, N 8.83. Found: C 65.71, H 8.67, N 8.80. [α]$^{25}$$_D$+4.7° (c =1.00, CHCl$_3$).

Example 6

(2S,9R)-2-[(tert-Butoxycarbonyl)amino]-11-amino-9-hydroxy-7-azaundecanoic Acid tert-Butyl Ester, Diacetate Salt (7)

The N$_\epsilon$ benzyl nitrile (6) (4.80 g, 10.7 mmol) was dissolved in glacial acetic acid (100 ml); 10% Pd—C (0.50 g) and PtO$_2$ (1.00 g) were added; and hydrogen gas was introduced. The reaction was complete after 6 hours, and the catalyst was filtered through a bed of Celite and washed with acetic acid. The filtrate was concentrated in vacuo. Azeotropic removal of the acetic acid with toluene gave (7) as a colorless oil (5.10 g, 99%). $^1$H NMR (500 MHz) (CD$_3$OD) δ 4.02–3.94 (m, 2H), 3.14–2.86 (m, 6H), 1.94 (s, 6H), 1.87–1.58 (m, 8H), 1.46 (s, 9H), 1.44 (s, 9H). $^{13}$C NMR (CD$_3$OD) δ 169.6, 156.54, 85.3, 70.2, 62.6, 56.6, 54.2, 53.9, 34.0, 31.1, 28.2, 26.3, 23.2. HRMS m/z calcd. for C$_{19}$H$_{40}$N$_3$O$_5$ 390.2968, found 390.2977. [α]$^{25}_D$+0.6° (c=1.00, CH$_3$OH).

Example 7

(2S,9R)-11-[(Benzyloxycarbonyl)amino]-2-[(tert-butoxycarbonyl)amino]-9-hydroxy-7-carbobenzyloxy-7-azaundecanoic Acid tert-Butyl Ester (8)

A solution of (7) (1.17 g, 2.30 mmol) in CHCl$_3$ (100 ml) was washed with saturated Na$_2$CO$_3$ solution. The aqueous layer was extracted with CHCl$_3$ (3×100 ml), and the combined organic layers were dried over Na$_2$SO$_4$ and concentrated in vacuo. A solution of the resultant oil (the free amine, 0.85 g, 2.18 mmol) in CH$_2$Cl$_2$ (60 ml) was cooled to 0° C. and treated with diisopropylethylamine (0.59 g, 4.57 mmol) and benzyl chloroformate (0.79 g, 4.60 mmol). The reaction mixture was stirred overnight at room temperature, concentrated to dryness and purified by flash chromatography (50% ethyl acetate/hexane) to give (8) (790 mg, 55%) as a colorless oil. $^1$H NMR (CDCl$_3$) δ 7.23 (m, 10H), 5.45 (m, 1H), 5.08 (s, 2H), 5.04 (s, 2H), 4.10 (m, 1H), 3.80 (m, 1H), 3.40 (m, 1H), 3.23 (m, 5H), 1.80–1.43 (m, 6H), 1.41 (s, 18H), 1.23 (m, 2H); $^{13}$C NMR (CDCl$_3$) δ 171.8, 157.5, 156.9, 155.3, 136.4, 128.4, 128.3, 127.9, 127.7, 81.6, 79.5, 69.2, 67.2, 66.5, 53.7, 48.5, 37.7, 34.8, 32.5, 28.2, 27.9, 22.3. HRMS m/z calcd. for C$_{35}$H$_{52}$N$_3$O$_9$ 658.3703, found 658.3774. [α]$^{24}_D$+4.6° (c=0.50, CHCl$_3$).

Example 8

(2S,9R)-11-[(Benzyloxycarbonyl)amino]-7-(carbobenzyloxy)-9-hydroxy-7-azaundecanoic Acid (9)

The ester (8) (500 mg, 0.76 mmol) was dissolved in a pre-made mixture of trifluoroacetic acid (1.12 g, 9.90 mmol), CH$_2$Cl$_2$ (2.05 g, 24.0 mmol) and triethylsilane (220 mg, 1.9 mmol) and stirred at room temperature for 20 hours. The reaction mixture was concentrated to dryness and stirred again in the pre-made mixture as described above for an additional 6 hours. The reaction mixture was concentrated, and the resultant oil was dissolved in 1.0 ml water and adjusted to pH 8 with saturated NaHCO$_3$ solution. The solution was concentrated and purified by chromatography on a C-18 column (55% acetone/water) to give 300 mg (78%) of (9) as a colorless oil. $^1$H NMR (CD$_3$OD) δ 7.40–7.25 (m, 10H), 5.11 (s, 2H), 5.06 (s, 2H), 3.82 (m, 1H), 3.55 (m, 1H), 3.40–3.10 (m, 6H), 1.95–1.30 (m, 8H). HRMS m/z calcd. for C$_{26}$H$_{36}$N$_3$O$_7$ 502.2553, found 502.2531. [α]$^{24}_D$+4.2° (c=1.00, CH$_3$OH).

Example 9

(2S,9R)-2-Amino-11-[(benzyloxycarbonyl)amino]-7-(carbobenzyloxy)-9-(tetrahydropyran-2-yloxy)-7-azaundecanoic Acid (10)

Trifluoroacetic acid (115 mg, 1.01 mmol) was added to a solution of (9) (265 mg, 0.53 mmol) in CHCl$_3$ (5 ml). The solution was concentrated in vacuo. The resultant oil was dissolved in dry CH$_2$Cl$_2$ (15 ml) and 3,4-dihyro-2H-pyran (51 mg, 55 μl, 0.61 mmol) was added at room temperature. The reaction progress was monitored by TLC, and three additional portions of 3,4-dihydro-2H-pyran (51 mg each) were added over the next 7 hours. The reaction mixture was stirred for an additional 12 hours and concentrated in vacuo. The oil was dissolved in water and methanol (1:1, 4 ml) and adjusted to pH 7 with saturated NaHCO$_3$ solution. The solution was concentrated, and the crude oil was purified by chromatography on a C-18 column (55% acetone/water) to give 210 mg (68%) of (10) as a colorless oil and 20 mg (8%) recovered starting material (9). $^1$H NMR (CD$_3$OD) δ 7.40–7.22 (m, 10H), 5.10 (m, 2H), 5.04 (s, 2H), 4.62–4.32 (m, 1H), 4.02–3.68 (m, 2H), 3.50 (m, 1H), 3.44–3.06 (m, 7H), 1.98–1.28 (m, 14H); $^{13}$C NMR (CD$_3$OD) δ 174.3, 158.7, 158.1, 138.5, 129.7, 129.6, 129.5, 129.3, 129.0, 128.8, 101.7, 100.1, 74.9, 68.3, 67.4, 65.3, 56.2, 48.4, 38.2, 34.3, 32.6, 32.1, 28.5, 26.4, 23.6, 21.8, 21.2. HRMS m/z calcd. for C$_{31}$H$_{43}$N$_2$O$_8$ 586.3128, found 586.3118. [α]$^{24}_D$+4.0° (c=0.25, CH$_3$OH).

Example 10

Sodium (2S,9R)-11-[(Benzyloxycarbonyl)amino]-7-(carbobenzyloxy)-2-[9-fluorenylmethoxy-carbonyl)amino-9-(tetrahydropyran-2-yloxy)-7-azaundecanoic Acid (11a)

A solution of 9-fluorenylmethyl N-succinimidyl carbonate (181 mg, 0.53 mmol) in DMF (2.5 ml) was added to a solution of (10) (210 mg, 0.36 mmol) in 9% Na$_2$CO$_3$ (0.836 ml, 0.72 mmol) at 0° C. and stirred overnight at room temperature. The pH was adjusted to 7 with 0.1 N HCl. The mixture was concentrated to an oil and purified by flash chromatography (90% CHCl$_3$/MeOH) to give (11a) (239 mg, 83%) as a colorless oil. $^1$H NMR (CDCl$_3$) δ 7.78 (m, 2H), 7.60 (m, 2H), 7.30 (m, 14H), 5.72 (m, 2H), 5.18 (s, 2H), 5.16 (s, 2H), 4.60 (m, 1H), 4.52–4.22 (m, 3H), 4.20 (m, 1H), 4.00–3.72 (m, 3H), 3.50–3.10 (m, 6H), 2.00–1.22 (m, 14H); $^{13}$C NMR (150 MHz) (CDCl$_3$) δ 174.6, 156.7, 156.4, 143.9, 143.8, 141.3, 136.8, 136.5, 128.5, 128.5, 128.1, 128.0, 127.9, 127.7, 127.1, 125.1, 124.9, 120.0, 100.7, 73.5, 67.4, 67.2, 66.6, 53.5, 48.4, 47.2, 32.9, 32.0, 31.5, 30.8, 28.0, 27.3, 25.2, 22.0, 21.1, 19.8. HRMS m/z calcd. for C$_{46}$H$_{53}$N$_3$O$_{10}$Na 830.3629, found 830.3661. Anal. calcd. for C$_{46}$H$_{53}$N$_3$O$_{10}$: C 68.38, H 6.61, N 5.20. Found: C 68.55, H 6.63, N 5.26. [α]$^{26}_D$+3.4° (c=1.00, CHCl$_3$).

Example 11

(2S,9S)-2-[(tert-Butoxycarbonyl)amino]-10-chloro-9-hydroxy-7-azadecanoic Acid tert-Butyl Ester (12a)

A solution of 3 (4.83 g, 14.3 mmol) in chloroform (100 mL) was extracted with saturated NaHCO$_3$ solution (2×100 mL) and water (100 mL). The organic layer was dried, concentrated, and further dried in vacuo. The resulting oil was dissolved in cyclohexane (26 mL), and (S)-(+)-epichlorohydrin (1.58 g, 17.1 mmol) was added under an Ar atmosphere. The precipitated product was filtered after 27 h, washed with cold cyclohexane, and dried in vacuo to give 12a (2.20 g, 39%) as a fine, white powder: mp 87–88° C.; $^1$H NMR δ 1.30–1.83 (m, 6H), 1.44 (s, 9H), 1.46 (s, 9H), 2.57–2.66 (m, 3H), 2.77 (dd, 1H, J=12.2, 3.9), 3.51 (dd, 1H, J=11.2, 5.7), 3.56 (dd, 1H, J=11.2, 5.2), 3.84–3.91 (m, 1H), 3.94 (dd, 1H, J=8.6, 5.3); $^{13}$C NMR δ 24.6, 28.3, 28.7, 30.0, 32.6, 48.2, 50.3, 53.5, 55.8, 71.1, 80.4, 82.5, 158.1, 173.8; HRMS m/z calcd for C$_{18}$H$_{36}$ClN$_2$O$_5$ 395.2313, found 395.2303. Anal. calcd. for C$_{18}$H$_{35}$ClN$_2$O$_5$: C$_{54.74}$, H 8.93, Cl 8.98, N 7.09. Found: C 54.80, H. 8.99, Cl 9.02, N 7.08 [α]$^{22}_D$−26.1° (c 1.00, CH$_3$OH).

Example 12

(2S,9R)-2-[(tert-Butoxycarbonyl)amino]-10-chloro-9-hydroxy-7-azadecanoic Acid tert-Butyl Ester (12b)

Compound 12b was prepared from reaction of 3 (5.93 g, 17.50 mmol) with (R)-(−)-epichlorohydrin (1.62 g, 17.50 mmol) in 44% yield using the same procedure as described for 12a. 12b: mp 101° C.; $^1$H NMR δ 1.30–1.80 (m, 6H), 1.44 (s, 9H), 1.46 (s, 9H), 2.61 (m, 3H), 2.77 (dd, 1H, J=12.3,4.0), 3.49 (dd, 1H, J=11.3, 5.8), 3.57 (dd, 1H, J=11.3, 5.3), 3.88 (m, 1H), 3.94 (dd, 1H, J =8.6, 5.0); HRMS m/z calcd for $C_{18}H_{36}ClN_2O_5$ 395.2313, found 395.2303. Anal. calcd. for $C_{18}H_{35}ClN_2O_5$: C 54.74, H 8.93, N 7.09. Found: C 54.63, H 8.82, N 7.10. $[α]^{22}_D$–15.5° (c 0.96, $CH_3OH$).

Example 13

(2S,9S)-2-[(tert-Butoxycarbonyl)amino]-7-(carbobenzyloxy)-10-chloro-9-hydroxy-7-azadecanoic Acid tert-Butyl Ester (13a)

A solution of benzyl chloroformate (1.21 g, 7.09 mmol) in chloroform (10 mL) was added over a period of 15 min to an ice-cold solution of 12a (2.16 g, 5.46 mmol) in chloroform (40 mL) under an Ar atmosphere. After dropwise addition of triethylamine (1.11 g, 11.0 mmol) in chloroform (10 mL), the reaction mixture was stirred for 4.5 hours at rt. The reaction mixture was extracted with 1 N HCl (60 mL) and water (60 mL), dried, and concentrated. The residue was purified by flash chromatography (33% ethyl acetate/hexane) to give 13a (2.69 g, 93%) as a colorless oil: $^1$H NMR 61.30–1.83 (m, 6H), 1.44 (s, 9H), 1.45 (s, 9H), 3.20–3.64 (m, 6H), 3.93 (dd, 1H, J=8.2; 5.5), 4.00 (m, 1H), 5.12 (s, 2H), 7.26–7.40 (m, 5H); $^{13}$C NMR δ 24.1, 24.3, 28.8, 32.5, 49.4, 51.4, 52.2, 55.7, 68.4, 71.0, 80.4, 82.5, 129.0, 129.1, 129.6, 138.0, 157.5–158.4 (br), 158.1, 173.7; HRMS m/z calcd for $C_{26}H_{42}ClN_2O_7$ 529.2681, found 529.2694. Anal. calcd. for $C_{26}H_{41}ClN_2O_7$: C 59.03, H 7.81, N 5.29. Found: C 59.09, H 7.78, N 5.21. $[α]^{23}_D$–21.8° (c 1.00, $CH_3OH$).

Example 14

(2S,9R)-2-[(tert-Butoxycarbonyl)amino]-7-(carbobenzyloxy)-10-chloro-9-hydroxy-7-azadecanoic Acid tert-Butyl Ester (13b)

According to the method described for the preparation of 13a, 12b (2.93 g, 7.42 mmol) was reacted with benzyl chloroformate (1.60 g, 9.38 mmol) and triethylamine (1.50 g, 14.81 mmol) to obtain 13b (3.35 g, 85%) as a colorless oil: $^1$H NMR δ 1.24–1.82 (m, 6H), 1.44 (s, 9H) 1.45 (s, 9H), 3.15–3.64 (m, 6H), 3.92 (m, 1H), 4.00 (m, 1H), 5.12 (m, 2H), 7.25–7.40 (m, 5H); $^{13}$C NMR δ 24.0, 28.3, 28.8, 32.5, 42.4, 51.3, 52.3, 55.7, 68.4, 71.0, 71.1, 80.4, 82.5, 129.0, 129.1, 129.6, 138.0, 158.1, 158.4, 173.7; HRMS m/z calcd for $C_{26}H_{42}ClN_2O_7$ 529.2681, found 529.2691. Anal. calcd. for $C_{26}H_{41}ClN_2O_7$: C 59.03, H 7.81, N 5.29. Found: C 58.88, H 7.83, N 5.23. $[α]^{23}_D$–1.7°(c 0.98, $CH_3OH$).

Example 15

(2S,9R)-2-[tert-(Butoxycarbonyl)amino]-7-(carbobenzyloxy)-10-cyano-9-hydroxy-7-azadecanoic Acid tert-Butyl Ester (14a).

A mixture of 13a (2.65 g, 5.02 mmol), dry KCN (3.45 g, 53.0 mmol), and 18-crown-6 (279 mg, 1.05 mmol) in dry acetonitrile (100 mL) was stirred at 60° C. for 16 hours under an Ar atmosphere. The reaction mixture was cooled, filtered through Celite, and concentrated. The residue was purified by flash chromatography (33% ethyl acetate/hexane, then 50% ethyl acetate/hexane) to give 14a (1.84 g, 70%) as a colorless oil: $^1$H NMR δ 1.25–1.80 (m, 6H), 1.44 (s, 9H), 1.45 (s, 9H), 2.42–2.76 (m, 2H), 3.20–3.58 (m, 4H), 3.92 (m, 1H), 4.08 (m, 1H), 5.13 (s, 2H), 7.26–7.48 (m, 5H); $^{13}$C NMR δ 24.0, 24.2, 28.2, 28.7, 32.4, 52.9, 53.8, 55.7, 67.1, 68.4, 80.4, 82.5, 118.9, 129.0, 129.2, 129.6, 138.0, 157.5–158.4 (br), 158.1, 173.7; HRMS m/z calcd for $C_{27}H_{42}N_3O_7$ 520.3023, found 520.3013. $[α]^{22}_D$–19.8° (c 1.00, $CH_3OH$).

Example 16

(2S,9S)-2-[(tert-Butoxycarbonyl)amino]-7-(carbobenzyloxy)-10-cyano-9-hydroxy-7-azadecanoic Acid tert-Butyl Ester (14b)

According to the method described for the preparation of 14a, 13b (3.23 g, 6.10 mmol) was reacted with KCN (3.96 g, 60.82 mmol) and 18-crown-6 (242 mg, 0.92 mmol) to obtain 14b (1.62 g, 51%) as a colorless oil: $^1$H NMR δ 1.20–1.84 (m, 6H), 1.44 (s, 9H), 1.45 (s, 9H), 2.55 (m, 2H), 3.20–3.50 (m, 4H), 3.92 (dd, 1H, J=8.2, 5.1), 4.07 (m, 1H), 5.13 (s, 2H), 7.26–7.41 (m, 5H); $^{13}$C NMR δ 24.1, 24.2, 28.3, 28.8, 32.4, 55.7, 67.1, 68.4, 80.4, 82.5, 118.9, 129.0, 129.2, 129.6, 138.0, 158.1, 173.7; HRMS m/z calcd for $C_{27}H_{42}N_3O_7$ 520.3023, found 520.3048. Anal. calcd. for $C_{27}H_{41}N_3O_7$: C 62.41, H 7.95, N 8.09. Found: C 62.14, H 7.95, N 7.97. $[α]^{22}_D$–5.3 (c 1.15, $CH_3OH$).

Example 17

(2S,9R)-2-[(tert-Butoxycarbonyl)amino]-11-amino-9-hydroxy-7-azaundecanoic Acid tert-Butyl Ester, Diacetate Salt (15a)

To a solution of 14a (1.74 g, 3.34 mmol) in glacial acetic acid (42 mL) was added 10% Pd—C (0.17 g) and $PtO_2$ (0.34 g), and $H_2$ gas was introduced. The catalyst was removed after 22 hours by filtration through Celite. The filtrate was concentrated in vacuo. Azeotropic removal of acetic acid with toluene provided 15a as a colorless oil (1.70 g, 100%): $^1$H NMR ($D_2O$) δ 1.44 (s, 9H), 1.47 (s, 9H), 1.50–1.90 (m, 8H), 1.97 (s, 6H), 3.00–3.25 (m, 6H), 3.97 (dd, 1H, J=8.8, 5.2), 4.06 (tt, 1H, J =9.6, 3.0); $^{13}$C NMR ($D_2O$, internal standard $CH_3OH$=49.5 ppm) δ 24.3, 24.5, 26.9, 29.3, 29.7, 32.1, 33.5, 38.5, 54.1, 56.5, 66.8, 83.5, 85.8, 159.8, 176.0, 182.0; HRMS m/z calcd for $C_{19}H_{40}N_3O_5$ 390.2968, found 390.2965. $[α]^{21}_D$–16.1° (c 1.00, $CH_3OH$).

Example 18

(2S,9S)-2-[(tert-Butoxycarbonyl)amino]-11-amino-9-hydroxy-7-azaundecanoic Acid tert-Butyl Ester, Diacetate Salt (15b)

According to the method described for the preparation of 15a, to a solution of 14b (172 mg, 0.33 mmol) in glacial acetic acid (5 mL) was added 10% Pd—C (17 mg) and $PtO_2$ (35 mg) under an $H_2$ atmosphere to obtain 15b in quantitative yield as a colorless oil: $^1$H NMR ($D_2O$) δ 1.30–2.00 (m, 8H), 1.45 (s, 9H), 1.48 (s, 9H), 1.92 (s, 6H), 2.99–3.28 (m, 6H), 3.99 (dd, 1H, J=9.0, 5.11), 4.06 (it, 1H, J=9.5, 3.3); HRMS m/z calcd for $C_{19}H_{40}N_3O_5$ 390.2968, found 390.2967. $[α]^{22}_D$–7.5° (c 1.03, $CH_3OH$).

Example 19

(2S,9R)-1-[(Benzyloxycarbonyl)amino]-2-[(tert-butoxycarbonyl)amino]-9-hydroxy-7-(carbobenzyloxy)-7-azaundecanoic Acid tert-Butyl Ester (16a)

A solution of 15a (1.20 g, 2.35 mmol) in water (35 mL) and diethyl ether (35 mL) was vigorously stirred and cooled to 0° C. under an Ar atmosphere. KHCO$_3$ (3.08 g, 30.8 mmol) was added, and then N-(benzyloxycarbonyloxy) succinimide (CBZ-ONSu, 1.70 g, 6.82 mmol) was added in 5 portions over 20 min. The reaction mixture was warmed to room temperature and stirred for 4 hours. The layers were separated; the aqueous layer was extracted with diethyl ether (2×35 mL). The combined ether layers were dried and concentrated. The residue was purified by flash chromatography (50% ethyl acetate/hexane) to give 16a (772 mg, 50%) as a colorless oil: $^1$H NMR δ 1.22–1.82 (m, 8H), 1.43 (s, 9H), 1.44 (s, 9H), 3.08–3.45 (m, 6H), 3.81 (m, 1H), 3.92 (m, 1H), 5.06 (s, 2H), 5.10 (s, 2H), 7.24–7.38 (m, 10H); $^{13}$C NMR δ 24.1, 28.3, 28.8, 32.5, 35.9, 38.6, 54.0, 54.7, 55.7, 67.4, 68.3, 69.0, 80.4, 82.5, 128.8, 128.9, 129.1, 129.4; 129.6, 138.1, 138.4, 158.1, 158.4, 158.9, 173.7; HRMS m/z calcd for C$_{35}$H$_{52}$N$_3$O$_9$ 658.3704, found 658.3767. Anal. calcd. for C$_{35}$H$_{51}$N$_3$O$_9$: C 63.91, H 7.81, N 6.39. Found: C 63.73, H 7.77, N 6.38.

Example 20

(2S,9S)-11-[(Benzyloxycarbonyl)amino]-2-[(tert-butoxycarbonyl)amino]-9-hydroxy-7-(carbobenzyloxy)-7-azaundecanoic Acid tert-Butyl Ester (16b)

According to the method described for the preparation of 16a, 15b (165 mg, 0.32 mmol) was reacted with CBZ-ONSu (178 mg, 0.71 mmol) to give 16b (90 mg, 43%) as a colorless oil: $^1$H NMR δ 1.18–1.82 (m, 8H), 1.43 (s, 9H), 1.44 (s, 9H), 3.06–3.48 (m, 6H), 3.83 (m, 1H), 3.92 (m, 1H), 5.05 (s, 2H), 5.10 (s, 2H), 7.22–7.40 (m, 10H); $^{13}$C NMR δ 24.1, 28.3, 28.8, 32.5, 35.9, 38.6, 49.3, 54.0, 54.7, 55.8, 67.4, 68.3, 69.0, 80.4, 82.5, 128.9, 128.9, 129.1, 129.4, 129.6, 138.1, 138.4, 158.0, 158.4, 158.9, 173.7; HRMS m/z calcd for C$_{35}$H$_{52}$N$_3$O$_9$ 658.3704, found 658.3702. Anal. calcd. for C$_{35}$H$_{51}$N$_3$O$_9$: C 63.91, H 7.81, N 6.39. Found: C 63.84, H 7.73, N 6.36. [α]$^{23}_D$ −5.2° (c 1.00, CH$_3$OH).

Example 21

(2S,9R)-2-Amino-11-[(benzyloxycarbonyl)amino]-7-(carbobenzyloxy)-9-hydroxy-7-azaundecanoic Acid (17a)

The ester 16a (766 mg, 1.16 mmol) was added to a mixture of trifluoroacetic acid (1.73 g, 15.1 mmol), CH$_2$Cl$_2$ (1.2 mL), and triethylsilane (4.37 g, 37.5 mmol) and stirred at room temperature for 21 hours under an Ar atmosphere. The reaction mixure was concentrated to dryness and stirred again in the mixture as described above for an additional 18 hours. The reaction mixture was concentrated; the resultant oil was dissolved in water (4.0 mL) and adjusted to pH 7 with saturated NaHCO$_3$ solution. The solution was concentrated, and the residue was purified by chromatography on a C-18 column (30% acetone/water, followed by 55% acetone/water) to give 17a (421 mg, 72%) as a colorless oil: $^1$H NMR (45° C) δ 1.31–1.99 (m, 8H), 3.10–3.46 (m, 6H), 3.52 (t, 1H, J=5.9), 3.83 (m, 1H), 5.06 (s, 2H), 5.10 (s, 2H), 7.22–7.36 (m,10H); $^{13}$C NMR δ 23.5, 28.4, 29.2, 32.0, 35.9, 38.6, 54.2, 54.9, 56.0, 67.4, 68.3, 69.0, 128.7, 128.8, 128.9, 129.1, 129.4, 129.5, 138.1, 138.4, 158.0, 158.3, 158.9, 174.5; HRMS m/z calcd for C$_{26}$H$_{36}$N$_3$O$_7$ 502.2553, found 502.2517. [α]$^{24}_D$ +5.0° (c 1.00, CH$_3$OH).

Example 22

(2S,9S)-2-Amino-11-[(benzyloxycarbonyl)amino]-7-(carbobenzyloxy)-9-hydroxy-7-azaundecanoic Acid (17b)

According to the method described for the preparation of 17a, 16b (78 mg, 0.12 mmol) was reacted with trifluoroacetic acid (704 mg, 6.20 mmol) and triethylsilane (140 mg, 11.92 mmol) in CH$_2$Cl$_2$ (0.98 mL) to give 17b (37 mg, 62%) as a colorless oil: $^1$H NMR δ 1.20–2.10 (m, 8H), 3.05–3.70 (m, 7H), 3.82 (m, 1H), 5.05 (s, 2H), 5.10 (s, 2H), 7.20–7.60 (m, 10H); HRMS m/z calcd for C$_{26}$H$_{36}$N$_3$O$_7$ 502.2553, found 502.2546. [α]$^{23}_D$ +3.6° (c 1.00, CH$_3$OH).

Example 23

(2S,9R)-2-Amino-11-[(benzyloxycarbonyl)amino]-7-(carbobenzyloxy)-9-(tetrahydropyran-2-yloxy)-7-azaundecanoic Acid (18a)

Trifluoroacetic acid (164 mg, 1.44 mmol) was added to a solution of 17a (360 mg, 0.72 mmol) in CHCl$_3$ (7 mL). The solution was concentrated in vacuo. The resultant oil was dissolved in CH$_2$Cl$_2$ (20 mL), and 3,4-dihydro-2H-pyran (69 mg, 75 μL, 0.83 mmol) was added at room temperature. The reaction progress was monitored by TLC, and six additional portions of 3,4-dihydro-2H-pyran (69 mg each) were added over the next 31 hours. The reaction mixture was stirred for an additional 16 hours and concentrated in vacuo. The oil was dissolved in water (4 mL) and methanol (8 mL), then adjusted to pH 7 with saturated NaHCO$_3$ solution. The solution was concentrated, and the crude oil was purified by chromatography on a C-18 column (30% acetone/water, followed by 55% acetone/water) to give 18a (219 mg, 52%) as a colorless oil: $^1$H NMR δ 1.20–1.98 (m, 14H), 3.06–3.56 (m, 8H), 3.68–4.02 (m, 2H), 4.33–4.62 (m, 1H), 5.06 (s, 2H), 5.11 (s, 2H), 7.24–7.36 (m, 10H); $^{13}$C NMR δ 20.7, 21.1, 21.7, 23.6, 26.3, 26.5, 32.0, 32.5, 34.2, 38.1, 38.5, 52.0, 56.2, 64.2, 65.2, 67.3, 68.3, 74.9, 100.1, 101.6, 128.79, 128.96, 129.02, 129.10, 129.20, 129.47, 129.56, 129.62, 138.3, 138.5, 158.0, 158.7, 174.8; HRMS m/z calcd for C$_{31}$H$_{43}$N$_3$NaO$_8$ 608.2948, found 608.2954.

Example 24

(2S,9S)-2-Amino-11-[(benzyloxycarbonyl)amino]-7-(carbobenzyloxy)-9-(tetrahydropyran-2-yloxy)-7-azaundecanoic Acid (18b)

According to the method described for the preparation of 18a, 17b (37 mg, 73.8 μmol) was reacted with trifluoroacetic acid (17 mg, 0.15 mmol) and 3,4-dihydro-2H-pyran (46 mg, 50 μL, 0.55 mmol) in CH$_2$Cl$_2$ (2 mL) to give 18b (25 mg, 58%) as a colorless oil: $^1$H NMR δ 1.26–1.96 (m, 14H), 3.02–4.04 (m, 10H), 4.32–4.63 (m, 1H), 5.06 (s, 2H), 5.11 (s br, 2H), 7.22–7.40 (m, 10H); HRMS m/z calcd for C$_{31}$H$_{44}$N$_3$O$_8$ 586.3128, found 586.3137.

Example 25

(2S,9R)-11-[(Benzyloxycarbonyl)amino]-7-(carbobenzyloxy)-2-[(9-fluorenylmethoxycarbonyl)amino]-9-(tetrahydropyran-2-yloxy)-7-azaundecanoic Acid (11a)

A solution of 9-fluorenylmethyl N-succinimidyl carbonate (203 mg, 0.60 mmol) in DMF (3.0 mL) was added to a solution of 18a (219 mg, 0.37 mmol) in 9% Na$_2$CO$_3$ (803 mg, 0.68 mmol) at 0° C. and stirred overnight at room temperature. The pH was adjusted to 7.0 with 0.1 N HCl. The mixture was concentrated to an oil and purified by flash chromatography (CHCl$_3$, then 95% CHCl$_3$/MeOH) to give 11a (150 mg, 50%) as a colorless oil: $^1$H NMR δ 1.15–1.94 (m, 14H), 3.10–3.52 (m, 7H), 3.66–3.98 (m, 2H), 4.05–4.21 (m, 2H), 4.24–4.61 (m, 3H), 5.04 (s, 2H), 5.08 (s, 2H), 7.21–7.40 (m, 14H), 7.65 (dd, 2H, J=6.9, 4.2), 7.77 (d, 2H, J=7.2); $^{13}$C NMR δ 21.1, 21.7, 24.1, 26.4, 26.5, 28.2, 28.9, 32.1, 32.5, 32.6, 33.2, 34.3, 38.1, 38.5, 51.9, 52.4, 55.5, 64.1, 65.2, 67.4, 67.9, 68.3, 74.9, 79.5, 100.0, 101.5, 120.9, 126.3, 128.2, 128.80, 128.97, 129.10, 129.20, 129.48, 129.57, 129.62, 138.2, 138.5, 142.6, 145.2, 145.4, 158.1, 158.6, 176.8; HRMS m/z calcd for $C_{46}H_{54}N_3O_{10}$ 808.3809, found 808.3833.

Example 26

(2S,9S)-11-[(Benzyloxycarbonyl)amino]-7-(carbobenzyloxy)-2-[(9-fluorenylmethoxycarbonyl)amino]-9-(tetrahydropyran-2-yloxy)-7-azaundecanoic Acid (11b)

According to the method described for the preparation of 11a, 18b (26 mg, 44 μmol) was reacted with 9-fluorenylmethyl N-succinimidyl carbonate (22 mg, 66 μmol) and $Na_2CO_3$ (9 mg, 88 μmol) to give 11b (20 mg, 55%) as a colorless oil: $^1$H NMR δ 1.14–1.96 (m, 14H), 3.04–3.55 (m, 6H), 3.64–3.98 (m, 3H), 4.14 (m, 1H), 4.20 (t, 1H, J=6.9), 4.34 (d, 2H, J=6.9), 4.38–4.61 (m, 1H), 5.05 (s, 2H), 5.09 (s, 2H), 7.20–7.42 (m, 14H), 7.65 (m, 2H), 7.78 (d, 2H, J=7.4); HRMS m/z calcd for $C_{46}H_{54}N_3O_{10}$ 808.3809, found 808.3839. Anal. calcd. for $C_{46}H_{53}N_3O_{10}$: $C_{68.38}$, H 6.61, N 5.20. Found: C 68.26, H 6.69, N 5.13.

Example 27

(2S,9R)-2-[(tert-Butoxycarbonyl)amino]-7-(carbobenzyloxyl)-10-cyano-9-[(S)-α-methoxy-α-(trifluoromethyl)phenylacetoxy]-7-azadecanoic Acid tert-Butyl Ester (19a)

The reaction was carried out in an oven-dried 5×175 mm NMR tube, fitted with a rubber septum, under an Ar atmosphere. The reagents were injected via syringe in the following order: anhydrous pyridine (300 μL), (R)-(−)-α-methoxy-α-trifluoromethyl-phenylacetic acid (Mosher's acid chloride, 13 μL, 70 μmol), anhydrous carbon tetrachloride (200 μL), and then a solution of 14a (27 mg, 52 μmol) in anhydrous carbon tetrachloride (500 μL). The reaction mixture was shaken and allowed to stand at room temperature for 18 hours. The reaction mixture was then taken up in chloroform (20 mL), extracted with saturated $NaHCO_3$ solution, and then extracted with saturated NaCl solution. The organic layer was dried and concentrated in vacuo. The residue was purified by flash chromatography (33% ethyl acetate/hexane) to give 19a (31 mg, 81%) as a colorless oil: $^1$H NMR ($CDCl_3$, 45° C.) δ 1.08–1.80 (m, 6H); 1.447 (s, 9H), 1.453 (s, 9H), 2.52–3.12 (m, 4H), 3.38 (dd, 1H, J=14.7, 6.7), 3.52 (dd, 1H, J=14.7, 4.6), 3.60 (s br, 3H), 4.08 (m, 1H), 4.92 (m,1H), 5.10 (s, 2H), 5.38 (m, 1H), 7.28–7.53 (m, 10H); $^{19}$F NMR (282 MHz, $CDCl_3$, $CFCl_3$ as internal standard, 45° C.) δ −71.86; HRMS m/z calcd for $C_{37}H_{49}F_3N_3O_9$ 736.3421, found 736.3367. $[α]^{22}_D$ −29.2° (c 1.00, $CHCl_3$)

Example 28

(2S,9S)-2-[tert-(Butoxycarbonyl)amino]-7-(carbobenzyloxy)-10-cyano-9-[(S)-α-methoxy-α-(trifluoromethyl)phenylacetoxy]-7-azadecanoic Acid tert-Butyl Ester (19b)

According to the method described for the preparation of 19a, 14b (24 mg, 46 μmol) was reacted with (R)-(−)-Mosher's acid chloride (14 mg, 55 μmol) to give 19b (23 mg, 69%) as a colorless oil: $^1$H NMR ($CDCl_3$, 45° C.) δ 1.14–1.80 (m, 6H), 1.44 (s, 9H), 1.45 (s, 9H), 2.54–2.92 (m, 2H), 3.09 (m, 1H), 3.27 (m, 1H), 3.46 (s br, 3H), 3.48 (dd, 1H, J=14.7, 6.9), 3.61 (dd, 1H, J=14.7, 5.1), 4.10 (m, 1H), 4.94 (m, 1H), 5.13 (s, 2H), 5.38 (m, 1H), 7.28–7.52 (m, 10H); $^{19}$F NMR (282 MHz, $CDCl_3$, $CFCl_3$ as internal standard, 45° C.) 6–71.85; HRMS m/z calcd for $C_{37}H_{49}F_3N_3O_9$ 736.3421, found 736.3443. $[α]^{22}_D$+16.10 (c 1.08, $CHCl_3$).

Example 29

FMOC-(2S,9R)-Hpu[$N^7$,$N^{12}$-di-CBZ, 9-(tetrahydropyran-2-yloxy)]-Val-O-t-Bu (20)

Under argon, 11a (66.8 mg, 82.7 μmol) and L-valine tert-butyl ester hydrochloride (21.6 mg, 103 μmol) were dissolved in DMF (9.3 mL) and stirred at 0° C. BOP reagent (42.4 mg, 95.9 mmol) was added, and the reaction mixture was stirred for 30 minutes before adding diisopropylethylamine (21.4 mg, 165 μmol) and allowing to warm to rt. After 21 h, the DMF was diluted with brine (40 mL) and extracted with ethyl acetate (3×30 mL). The ethyl acetate layer was then washed with 20 mL of each of the following: 1:1 10% citric acid/brine, brine, 1:1 saturated $NaHCO_3$/brine, and brine. The ethyl acetate was dried and evaporated, and the residue was purified by flash chromatography (2% MeOH/$CHCl_3$) to give 20 (66.0 mg, 83%) as a colorless oil: $^1$H NMR δ 0.94 (d, 6H, J=6.8), 1.20–1.88 (m, 14H), 1.44 (s, 9H), 2.11 (m, 1H), 3.13–3.49 (m, 8H), 3.66–3.98 (m, 2H), 4.05–4.24 (m, 2H), 4.28–4.62 (m, 3H), 5.05 (s, 2H), 5.09 (s, 2H), 7.22–7.41 (m, 14H), 7.64 (m, 2H), 7.77 (d, 2H, J=7.5).

Example 30

(2S,9R)-Hpu]$N^7$,$N^{12}$-di-CBZ, 9-(tetrahydropyran-2-yloxy)J-Val-O-t-Bu (21)

The fully protected dipeptide 20 (141.6 mg, 147.0 μmol) was dissolved in a solution of piperidine (2.0 mL) and DMF (20 mL) and stirred under argon for 4.5 hours. Concentration and purification by flash chromatography (2% MeOH/$CHCl_3$) gave 21 (97 mg, 89%) as a colorless oil: $^1$H NMR δ 0.96 (d, 6H, J=6.8), 1.22–1.84 (m, 14H), 1.44 (s, 9H), 2.13 (m, 1H), 3.04–3.49 (m, 8H), 3.68–4.00 (m, 2H), 4.20 (d, 1H, J=5.7), 4.35–4.63 (m, 1H), 5.06 (s, 2H), 5.11 (s, 2H), 7.24–7.38 (m, 10H); $^{13}$C NMR δ 18.5, 19.5, 21.7, 23.8, 26.4, 28.3, 32.0, 36.2, 36.9, 38.5, 55.7, 59.6, 64.0, 67.3, 68.2, 74.7, 82.8, 99.8, 101.5, 128.77, 128.94, 129.18, 129.46, 129.54, 129.60, 138.2, 138.5, 158.0, 158.6, 172.2, 177.6; HRMS m/z calcd for $C_{40}H_{61}N_4O_9$ 741.4438; found 741.4458.

Example 31

(2S,9R)-Hpu($N^7$,$N^{12}$-di-CBZ)-Val-O-t-Bu (22)

The free amine 21 (92 mg, 124 μmol) was dissolved in acetone (10 mL) and $H_2O$ (1.0 mL). Under argon, p-toluenesulfonic acid monohydrate (64 mg, 0.34 μmol) was added, and the solution was heated and stirred at 45° C. for 2 hours. The reaction mixture was diluted with $H_2O$ (10 mL), and the pH was adjusted to 7–8 with saturated $NaHCO_3$. The acetone was evaporated under vacuum, and the remaining aqueous layer was extracted with chloroform (2×10 mL). Drying, evaporation, and high-vacuum drying of the organic layer gave 22 (66.7 mg, 82%) as a colorless oil: $^1$H NMR δ 0.95 (d, 6H, J=6.8), 1.22–1.83 (m, 8H), 1.45 (s, 9H), 2.12 (m, 1H), 3.10–3.46 (m, 7H), 3.82 (m, 1H), 4.20 (d, 1H, J=5.7), 5.05 (s, 2H), 5.10 (s, 2H), 7.24–7.38 (m, 10H); $^{13}$C NMR δ 18.4, 19.5, 23.8, 28.3, 29.4, 31.9, 36.0, 36.9, 38.6, 54.6, 55.7, 59.6, 67.3, 68.2, 69.0, 82.8, 128.78, 128.87, 128.91, 129.05, 129.44, 129.55, 138.1, 138.4, 158.1, 158.9, 172.2, 177.7; HRMS m/z calcd for $C_{31}H_{53}N_4O_8$ 657.3863, found 657.3928.

Example 32

BOC-(2S,9R)-Hpu($N^7,N^{12}$-di-CBZ)-Val-O-t-Bu (23a)

Under argon, 22 (50.9 mg, 77.5 mmol) was dissolved in dioxane (2 mL) and $H_2O$ (1 mL) and cooled to 0° C. Di-tert-butyl dicarbonate (30 mg, 0.13 mmol) was added; the solution was allowed to stir 5 min, then warmed to room temperature and stirred 5 hours. Concentration followed by flash chromatography (2.5% MeOH/CHCl$_3$) gave 23a (58 mg, 99%) as a colorless oil: $^1$H NMR δ 0.94 (d, 6H, J=6.8), 1.22–1.83 (m, 8H), 1.43 (s, 9H), 1.45 (s, 9H), 2.12 (m, 1H), 3.10–3.42 (m, 6H), 3.82 (m, 1H), 4.06 (m, 1H), 4.20 (d, 1H, J=5.7), 5.06 (s, 2H), 5.10 (s, 2H), 7.23–7.37 (m, 10H); $^{13}$C NMR δ 18.4, 19.5, 24.0, 27.5, 28.3, 28.7, 32.0, 35.8, 38.6, 54.4, 55.8, 59.6, 67.4, 68.3, 68.8, 80.6, 82.8, 128.80, 128.87, 128.94, 129.06, 129.44, 129.56, 138.1, 138.4, 157.9, 158.3, 158.9, 172.0, 175.2. HRMS m/z calcd for $C_{40}H_{61}N_4O_{10}$ 757.4387, found 757.4396.

Example 33

BOC-(2S,9R)-Hpu[$N^7,N^{12}$di-CBZ,9-(S)-α-methoxy-α-trifluoromethylphenylacetoxy]-Val-O-t-Bu (24a)

Under argon, anhydrous pyridine (900 μL), anhydrous CCl$_4$ (600 μL), and (R)-(–)-Mosher's acid chloride (20 μL, 27 mg, 107 μmol) were mixed with vigorous stirring. A solution of 23a (55 mg, 73 μmol) in CCl$_4$ (1.5 mL) was added. After 17 hours of stirring at room temperature, the solution was diluted with chloroform (25 mL) and extracted with 25 mL of each of the following: brine; 1:1 1 N HCl/brine; brine; 1:1 saturated NaHCO$_3$/brine; and brine. The organic layer was dried and concentrated. Purification by flash chromatography (2:1 hexane/ethyl acetate) gave 24a (55 mg, 78%) as a colorless oil: $^1$H NMR (CDCl$_3$, 45.0° C.) δ 0.91 (d, 3H, J=6.8), 0.92 (d, 3H, J=6.8), 1.10–1.94 (m, 8H), 1.44 (s, 9H), 1.46 (s, 9H), 2.14 (m, 1H), 2.72–3.54 (m, 7H), 3.50 (s, 3H), 4.01 (m, 1H), 4.38 (dd, 1H, J=8.7, 4.7), 4.83–5.37 (m, 2H), 5.09 (s, 2H), 5.10 (s, 2H), 6.54 (m, 1H), 7.24–7.52 (m, 15H); $^{13}$C NMR (CDCl$_3$, 20° C.) δ 17.5, 18.8, 22.5, 26.7, 28.0, 28.3, 31.3, 32.3, 37.1, 54.3, 55.5, 57.4, 66.7, 67.3, 73.3, 79.9, 81.9, 84.6, 127.05, 127.88, 128.06, 128.23, 128.47, 128.53, 129.6, 131.8, 136.2, 136.5, 155.6, 155.9; 156.3, 166.6, 170.7, 171.8. $^{19}$F NMR (282 MHz, CDCl$_3$, CFCl$_3$=0 ppm) δ –71.78. HRMS m/z calcd for $C_{50}H_{68}F_3N_4O_{12}$ 973.4786, found 973.4867. $[α]^{21}_D$ –16.0° (c 0.50, CHCl$_3$).

Example 34

(2S,9R)-Hypusinyl-L-valine (25a)

Under argon, phenol (270 mg), pentamethylbenzene (250 mg), and 23a (10 mg, 13 μmol) were dissolved in TFA (5 mL) at 0° C. With vigorous stirring, triisopropylsilane (200 μL) and 30% HBr/HOAc (200 μL) were added, and the solution was allowed to stir 5 min before being warmed to room temperature and stirred an additional 55 min. After concentration, the reaction mixture was diluted with 10% HOAc/$H_2O$ (10 mL), and extracted three times with methyl tert-butyl ether (25 mL). Evaporation of the aqueous layer gave 25a (8 mg) as an oil: $^1$H NMR ($D_2O$, NaTSP external reference) δ 0.98 (d, 3H, J=6.8), 0.99 (d, 3H, J=6.8), 1.49 (m, 2H), 1.69–2.01 (m, 6H), 2.22 (m, 1H), 3.01–3.26 (m, 6H), 4.07 (tt, 1H, J=9.7, 3.1), 4.13 (t, 1H, J=6.6), 4.32 (d, 1H, J=5.7). HRMS mlz calcd for $C_{15}H_{33}N_4O_4$ 333.2502, found 333.2506.

Example 35

(2S,9S)-11-[(Benzyloxycarbonyl)amino]-2-[(tert-butoxycarbonyl)amino]-9-hydroxy-7-(carbobenzyloxy)-7-azaundecanoic Acid (26)

A solution of 17b (37 mg, 74.0 μmol) in 1,4-dioxane (2 mL) and water (1 mL) was cooled to 0° C., and 1 N NaOH (74 μmol) and di-tert-butyl dicarbonate (18 mg, 82.5 μmol) were added. The reaction mixture was stirred at room temperature for 2.5 hours. The organic solvent was removed under reduced pressure; the residue was taken up in ethyl acetate (4 mL) and water (4 mL), and cooled to 0° C. This mixture was acidified to pH 2–3 with 1 N KHSO$_4$ solution under stirring. The layers were separated, the aqueous layer was extracted with ethyl acetate (3×5 mL), and the combined organic layers were dried. Concentration in vacuo followed by flash chromatography (10% methanol/chloroform) gave 26 (33 mg, 74%) as a colorless oil: $^1$H NMR δ 1.25–1.95 (m, 8H), 1.44 (s, 9H), 3.06–3.50 (m, 6H), 3.83 (br m, 1H), 4.04 (br m, 1H), 5.06 (s, 2H), 5.10 (s, 2H), 7.22–7.44 (m, 10H). HRMS m/z calcd for $C_{31}H_{44}N_3O_9$ 602.3078, found 602.3053. $[α]^{21}_D$ +3.6° (c 1.00, CH$_3$OH).

Example 36

BOC-(2S,9S)-Hpu($N^7, N^{12}$-di-CBZ)-Val-O-t-Bu (23b)

A solution of 26 (31 mg, 51.5 μmol) and L-valine tert-butyl ester hydrochloride (12 mg, 57 μmol) in dry DMF (3 mL) was cooled to 0° C. under an Ar atmosphere. BOP (25 mg, 57 μmol) was added, and after 45 min DIEA (18 μL, 103 μmol) was added. The solution was warmed to room temperature and stirred overnight. The reaction mixture was diluted with saturated NaCl solution and extracted with ethyl acetate (3×30 mL). The combined organic layers were successively washed with ice-cold 10% citric acid/brine (1:1, 20 mL), brine (20 mL), saturated NaHCO$_3$ solution/brine solution (1:1, 20 mL), and brine (20 mL). The organic layer was dried and concentrated in vacuo. The residue was purified by flash chromatography (98% chloroform/methanol, then 95% chloroform/methanol) to yield 23b (23 mg, 59%) as a colorless oil: $^1$H NMR 60.95 (d, 6H, J=6.8), 1.25–1.85 (m, 8H), 1.43 (s, 9H), 1.45 (s, 9H), 2.12 (m, 1H), 3.08–3.48 (m, 6H), 3.82 (m, 1H), 4.05 (m, 1H), 4.20 (d, 1H, J=5.7), 5.06 (s, 2H), 5.11 (s, 2H), 7.22–7.42 (m, 10H). HRMS mlz calcd for $C_{40}H_{61}N_4O_{10}$ 757.4388, found 757.4387. $[α]^{21}_D$ –13.9° (c 1.17, CH$_3$OH).

Example 37

BOC-(2S,9S)-Hpu($N^7,N^{12}$-di-CBZ,9-[S-α-methoxy-α-(trifluoromethyl)phenylacetoxy])-Val-O-t-Bu (24b)

The reaction was carried out according to the procedure described for the synthesis of 24a, starting with 23b (18.6 mg, 24.6 μmol) and (R)-(–)-Mosher's acid chloride (10 μL, 54 μmol). After work-up, the residue was purified by flash chromatography (33% ethyl acetate/hexane) to give 24b (15 mg, 63%) as a colorless oil: $^1$H NMR (CDC$_3$, 45° C.) 60.90 (d, 3H, J=6.8), 0.93 (d, 3H, J=6.8),1.20–1.90 (m, 8H), 1.44

(s, 9H), 1.45 (s, 9H), 2.14 (m, 1H), 3.02 (m, 2H), 3.14–3.58 (m, 4H), 3.44 (s, 3H), 4.02 (m, 1H), 4.38 (dd, 1H, J=8.8, 4.6), 4.80–5.20 (m, 2H), 5.09 (s, 2H), 5.09 (s, 2H), 6.52 (m, 1H), 7.14–7.54 (m, 15H); $^{19}$F NMR (282 MHz, CDCl$_3$, CFCl$_3$ as internal standard, 45° C.) δ −71.40. HRMS m/z calcd for $C_{50}H_{68}F_3N_4O_{12}$ 973.4786, found 973.4739. $[α]^{23}_D$ −1.6° (c 0.50, CHCl$_3$).

Example 38

(2S,9S)-Hypusinyl-L-valine (25b)

An aliquot of 23b (7.3 mg, 9.6 μmol), phenol (250 mg), and pentamethylbenzene (250 mg) were dissolved in degassed TFA (5.0 mL) at 0° C. Triisopropylsilane (0.1 mL) and a saturated solution of HBr in acetic acid (0.2 mL) were added under an argon atmosphere. The solution was stirred at room temperature for 1 hour and concentrated under reduced pressure. The residue was dissolved in 10% acetic acid (10 mL) and extracted with methyl tert-butyl ether (3×25 mL). The aqueous layer was concentrated and dried in vacuo to give 25b (6.0 mg) as a colorless oil. $^1$H NMR δ 0.96 (d, 3H, J=6.8), 0.97 (d, 3H, J=6.8), 1.47 (m, 2H), 1.68–2.01 (m, 6H), 2.20 (m, 1H), 2.99–3.25 (m, 6H), 4.06 (tt, 1H, J=9.7, 3.1), 4.11 (t, 1H, J=6.4), 4.26 (d, 1H, J=5.7). HRMS m/z calcd for $C_{15}H_{33}N_4O_4$ 333.2502, found 333.2499.

I claim:

1. A method of synthesizing a hypusine derivative comprising:

a. providing an ester of $N_ε$-, $N_α$-diprotected L-lysine, said ester having the formula:

(a)

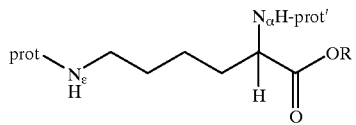

wherein prot and prot' are mutually orthogonal amino-protective groups and R is the residue of an esterifying alcohol which is orthogonal with respect to prot and prot', b. removing prot from $N_ε$ of (a) to produce a compound of the formula:

(b)

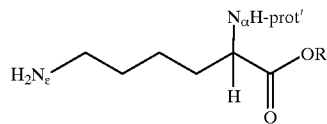

c. converting the compound of formula (b) to a chlorohydrin of the formula:

(j)

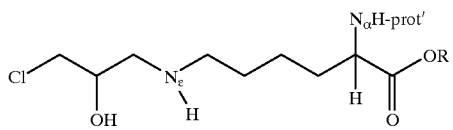

d. converting the compound of formula (j) to an $N_ε$-protected chlorohydrin of the formula:

(k)

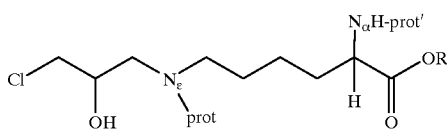

e. displacing the Cl group of (k) with CN to produce a nitrile of the formula:

(l)

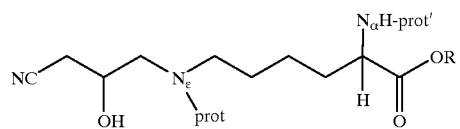

f. deprotecting the $N_ε$ group and converting the CN group of (l) to an amine group to produce the amino alcohol of the formula:

(f)

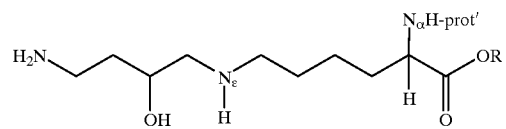

g. acylating the free amino groups of (f) to provide a di-N-protected $N_α$-protected L-lysine ester of the formula:

(g)

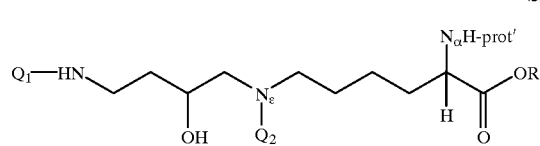

h. removing R and prot' of (g) to produce a compound of the formula:

(h)

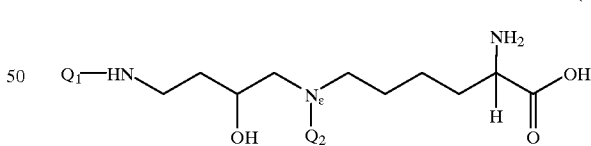

and i. acylating the free amino group and protecting the OH group to produce the hypusine derivative (1) of claim 1.

2. The method of claim 1 wherein ester (a) is provided by esterifying the $N_ε$-, $N_α$-diprotected L-lysine, and wherein prot is carbobenzyloxy, prot' is BOC and R is t-butyl.

3. The method of claim 1 wherein prot is removed from (a) by hydrogenation.

4. The method of claim 1 wherein (b) is converted to said (2S,9S) chlorohydrin (j) by $N_ε$-alkylation of (b) with (S)-epichlorohydrin or to said (2S,9R) chlorohydrin (j) by $N_ε$-alkylation of (b) with (R)-epichlorohydrin.

5. The method of claim 1 wherein said alkylation with (S)-epichlorohydrin is conducted at substantially room temperature.

6. The method of claim 1 wherein prot of said chlorohydrin (k) is carbobenzyloxy.

7. The method of claim 1 wherein said Cl group of (k) is displaced with CN by reaction of (k) with an alkali metal cyanide reactive therewith.

8. The method of claim 1 wherein (I) is $N_\epsilon$-deprotected and the CN group thereof converted to an amino group by catalytic hydrogenation.

9. The method of claim 8 wherein said hydrogenation is conducted in the presence of a mixture of palladium/charcoal and $PtO_2$.

10. The method of claim 1 wherein the free amino groups of (f) are acylated with a reactive carbobenzyloxycarboxylic acid derivative to produce (g) wherein $Q_1$ and $Q_2$ are each carbobenzyloxy groups.

11. The method of claim 10 wherein said reactive carbobenzyloxycarboxylic acid is N-(benzyloxycarbonyloxy)-succinimide.

12. The method of claim 1 wherein R and prot' are removed by reaction with trifluoroacetic acid in the presence of triethylsilane.

13. The method of claim 1 wherein the free amino group of (h) is acylated with 9-fluorenylmethyl-N-succinimidyl carbonate to produce a hypusine reagent wherein $Q_3$ is fluorenylmethoxycarbonyl and the hydroxy group of (h) is etherified with 3,4-dihydro-2H-pyran.

* * * * *

UNITED STATES PATENT AND TRADEMARK OFFICE
CERTIFICATE OF CORRECTION

PATENT NO. : 6,248,866 B1
DATED : June 19, 2001
INVENTOR(S) : Raymond J. Bergeron, Jr.

It is certified that error appears in the above-identified patent and that said Letters Patent is hereby corrected as shown below:

<u>Column 23, claim 6,</u>
Line 5, delete "(k)" and insert -- (d) --.

Signed and Sealed this

Twenty-sixth Day of March, 2002

Attest:

Attesting Officer

JAMES E. ROGAN
*Director of the United States Patent and Trademark Office*